United States Patent
Ganick et al.

(10) Patent No.: US 11,425,803 B2
(45) Date of Patent: Aug. 23, 2022

(54) PREDICTIVE SMART LIGHT CONTROL

(71) Applicant: LEDVANCE LLC, Wilmington, MA (US)

(72) Inventors: Aaron Ganick, Boxford, MA (US); Shiyong Zhang, Boxborough, MA (US)

(73) Assignee: LEDVANCE LLC, Wilmington, MA (US)

( * ) Notice: Subject to any disclaimer, the term of this patent is extended or adjusted under 35 U.S.C. 154(b) by 0 days.

(21) Appl. No.: 16/152,537

(22) Filed: Oct. 5, 2018

(65) Prior Publication Data
US 2021/0029789 A1 Jan. 28, 2021

(51) Int. Cl.
*G06N 3/08* (2006.01)
*H05B 47/19* (2020.01)
(Continued)

(52) U.S. Cl.
CPC ........... *H05B 45/20* (2020.01); *A61N 5/0618* (2013.01); *G06N 3/08* (2013.01); *G06N 5/022* (2013.01);
(Continued)

(58) Field of Classification Search
CPC .. H05B 33/086; H05B 33/0842; H05B 33/08; H05B 33/0803; H05B 33/0854; H05B 33/0857; H05B 33/0863; H05B 33/0869; H05B 33/0896; H05B 37/0227; H05B 37/0218; H05B 37/0281; H05B 37/0245; H05B 37/0272; H05B 37/029; H05B 37/0236; H05B 37/0263; H05B 37/02; H05B 37/0209; H05B 37/0254; H05B 45/20; H05B 45/22; H05B 47/19;
(Continued)

(56) References Cited

U.S. PATENT DOCUMENTS 8,933,638 B2 * 1/2015 Maxik .................. H05B 47/165
315/210
8,975,819 B2 3/2015 Iemmers
(Continued)

FOREIGN PATENT DOCUMENTS

WO WO2016088006 A1 6/2016

OTHER PUBLICATIONS

Naran Athmaraman, "Adaptive Predictive Traffic Timer Control Algorithm", https://www.cs.uic.edu/~nathmara/AthmaramanTraffic.pdf.

*Primary Examiner* — Jason Crawford
(74) *Attorney, Agent, or Firm* — Tutunjian & Bitetto PC

(57) ABSTRACT

In one aspect, a method for controlling lighting is provided. In one embodiment, the method includes setting an initial setting for lighting characteristics for light emitted by lighting devices; and recording user adjustments to the lighting characteristic from the initial setting as user data. The method further includes analysis of the user data with a remote light setting computing system to determine a lighting model for providing a predictive light characteristic light setting in response to an environment factor based input; and inputting environmental factors into the model produced by the remote light setting computing system to provide a predictive light characteristic setting. Light being emitted from the light emitting devices is then adjusted to the predictive light characteristics using a local controller in response to a user lighting request.

19 Claims, 11 Drawing Sheets

(51) Int. Cl.
*A61N 5/06* (2006.01)
*H05B 47/105* (2020.01)
*H05B 47/11* (2020.01)
*H05B 47/175* (2020.01)
*H05B 45/20* (2020.01)
*G06N 5/02* (2006.01)
*H05B 45/22* (2020.01)
*H05B 47/16* (2020.01)
*A61M 21/00* (2006.01)

(52) U.S. Cl.
CPC .......... *H05B 45/22* (2020.01); *H05B 47/105* (2020.01); *H05B 47/11* (2020.01); *H05B 47/16* (2020.01); *H05B 47/175* (2020.01); *H05B 47/19* (2020.01); *A61M 2021/0044* (2013.01); *A61N 2005/0651* (2013.01)

(58) Field of Classification Search
CPC ...... H05B 47/10; H05B 47/105; H05B 47/11; H05B 47/115; H05B 47/16; H05B 47/17; G06N 3/08; G06N 5/022; A61N 5/06; A61N 5/0613; A61N 5/0618; A61N 2005/0651; A61N 2005/0663; A61M 21/00; A61M 2021/0044; A61M 2021/0083
See application file for complete search history.

(56) References Cited

U.S. PATENT DOCUMENTS

| | | | |
|---|---|---|---|
| 9,827,439 B2* | 11/2017 | Maxik | A61N 5/0618 |
| 10,420,184 B1* | 9/2019 | Soler | G06F 3/04847 |
| 2011/0031806 A1* | 2/2011 | Altonen | E06B 9/68 |
| | | | 307/32 |
| 2012/0098439 A1* | 4/2012 | Recker | H05B 33/0815 |
| | | | 315/152 |
| 2012/0206050 A1* | 8/2012 | Spero | B60Q 1/1423 |
| | | | 315/152 |
| 2013/0085615 A1* | 4/2013 | Barker | A61G 10/00 |
| | | | 700/277 |
| 2014/0375222 A1* | 12/2014 | Rains, Jr. | G01J 3/50 |
| | | | 315/158 |
| 2015/0195883 A1* | 7/2015 | Harris | H05B 45/12 |
| | | | 315/155 |
| 2017/0238401 A1* | 8/2017 | Sadwick | H05B 47/195 |
| | | | 315/294 |
| 2017/0259079 A1* | 9/2017 | Grajcar | A01G 7/045 |
| 2018/0160490 A1* | 6/2018 | Li | H05B 47/16 |
| 2018/0318602 A1* | 11/2018 | Ciccarelli | A61M 21/02 |
| 2019/0209806 A1* | 7/2019 | Allen | G16H 20/70 |
| 2020/0229286 A1* | 7/2020 | Summers | G06V 40/20 |
| 2021/0003452 A1* | 1/2021 | Ashdown | H05B 47/175 |
| 2021/0029789 A1* | 1/2021 | Ganick | G06N 3/08 |

* cited by examiner

PREDICTIVE SMART LIGHT CONTROL

TECHNICAL FIELD

The present disclosure generally relates to controls and interfaces with lighting, and more particularly to methods of predicting light characteristic settings for a lighting environment.

BACKGROUND

Home and professional environments can contain many controllable lighting devices for creation of ambient, atmosphere, accent or task lighting. These controllable lighting devices are often connected and controlled via a network, which can be wired or wireless. These lighting devices can be controlled individually or in groups via a user interface of a lighting control.

SUMMARY

In one aspect, a method for controlling lighting is provided that produces predictive light characteristic settings. In one embodiment, the method includes setting an initial setting for lighting characteristics for light emitted by lighting devices; and recording user adjustments to the lighting characteristic from the initial setting as user data. The method further includes analysis of the user data with a remote light setting computing system to determine a lighting model for providing a predictive light characteristic light setting in response to an environment factor based input; and inputting environmental factors into the model produced by the remote light setting computing system to provide the predictive light characteristic setting. Light being emitted from the light emitting devices is then adjusted to the predictive light characteristics setting using a local controller in response to a user lighting request.

In another aspect, a system for controlling lighting is provided that produces predictive light characteristic settings. In one embodiment, the system for controlling lighting includes a local controller for sending commands to control light emissions from at least one light emitting device, and for recording user adjustments to the lighting characteristics of the light emissions from the at least one light emitting device from an initial setting as user data. The system for controlling lighting may also include a remote light setting computing device for analyzing the user data received from the local controller. The remote light setting computing device analyzes the user data to provide a lighting model for providing a predictive light characteristic setting in response to an environment factor based input. The remote light setting computing device transmits the predictive light characteristic setting to the local controller for the commands to control light emissions from the at least one light emitting device.

In yet another aspect, a computer program product is provided. In one embodiment, the computer program product includes a non-transitory computer readable storage medium including contents that are configured to cause a computer to perform a method for controlling lighting, the method including setting an initial setting for lighting characteristics for light emitted by lighting devices; and recording user adjustments to the lighting characteristic from the initial setting as user data. The method may further include analysis of the user data with a remote light setting computing system to determine a lighting model for providing a predictive light characteristic setting in response to an environment factor based input; and inputting environmental factors into the model produced by the remote light setting computing system to provide a predictive light characteristic setting. Thereafter, the light being emitted from the light emitting devices is adjusted to the predictive light characteristic setting using a local controller in response to a user lighting request.

BRIEF DESCRIPTION OF THE DRAWINGS

The following description will provide details of embodiments with reference to the following figures wherein.

DETAILED DESCRIPTION

Figure 1:
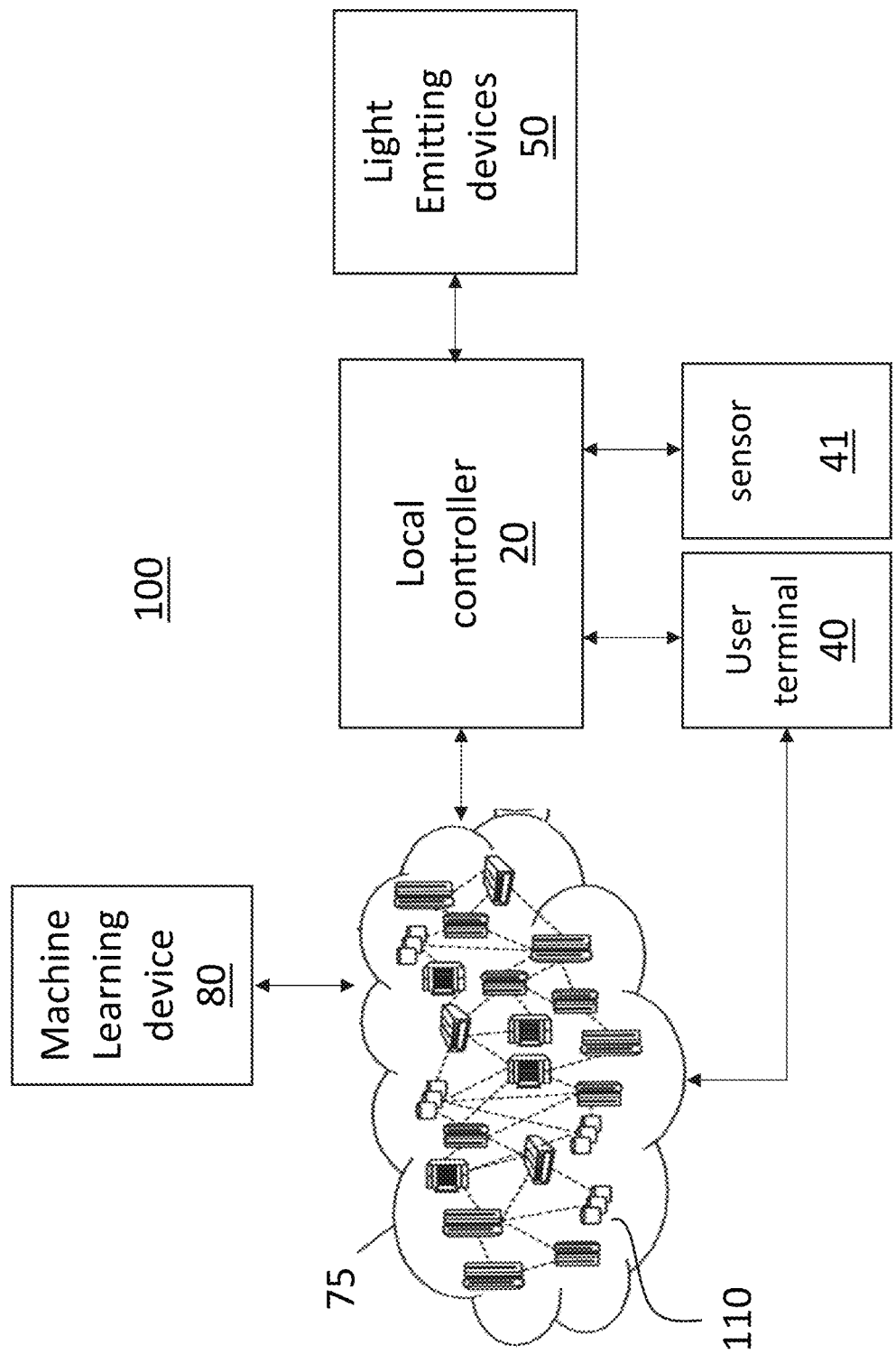
FIG. 1 is an illustration (block diagram) of an exemplary lighting system for a predictive lighting control that is responsive to data indicative of user actions, the lighting system including a remote computing system for receiving lighting data based on user actions and in response to the lighting data provides a predictive lighting setting, and a local controller that receives the predictive lighting setting for actuating light emitting devices to emit light having the characteristics of the predictive light setting.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

In some embodiments, the methods, systems and computer program products that are described herein can provide lighting characteristic adjustments in lighting systems by employing predictive or optimized light settings that are determined at a remote server based upon data collected for the user of the lighting system, e.g., time periods of typical lighting, e.g., lighting usage; calendar and season, e.g., day light saving; geographic location of the lighting system; and/or application of the lighting, e.g., research/office settings and on demand lighting treatments.

Light setting for lighting systems generally need customization to achieve an optimized lighting experience. Traditionally, the most popular way of customizing light settings is to incorporate dimmer switches into light circuits. As ambient light and activity changes, to achieve improved lighting experience, users need to change light settings frequently. Smart device based light control dives user convenience to control lights by performing the control at an easily accessible smart device rather than going to wall mounted switches, such as dimmer switches.

In some embodiments, the methods, systems and computer program products of the present disclosure enhances user convenience to the next level by: 1) predicting the light needs of the user; and 2) performing optimized light control without laborious user interventions. A predictive system is need that is responsive to the light system user's needs and actions. Reactive systems exist. For example, sensor based light control can detect, and then act accordingly. Examples of sensor based light controls include light sensor based light control and occupancy sensory based light control. Light sensor based control is a closed loop system where the controller adjusts lamp light output so that their target level is reached. Occupancy sensor based light control turns the lights on and off, or dims the lights in some circumstances, according to detected occupancy. These sensor based light controls can detect and then act accordingly. The drawback is that these systems do not predict, and therefore can not act ahead.

It has also been determined that pre-programmed light controls are not responsive to the light user's needs and actions. Not like light sensor based light control, pure pre-programmed light control is an open loop system. In pre-programmed light control, the target levels (including on an off) are determined according to a pre-programmed schedule which is time sequential in nature. These systems are not responsive to the light user's needs and actions. Any type of schedule changes require that the user will have to override or re-program the system. Further, because the control is schedule based, the only variable the system relies on is time. What is needed is a system that can learn from the user the user's needs in lighting characteristics and automatically adjust to meet those requirements without needing user interaction to reprogram the system, and the user's needs are to include greater variables than only the time of a schedule.

In other examples of light control systems, conditional actions, which may be referred to as applets, can allow the user of a light system to program light characteristics in response to the conditional actions. These rules may be referred to as "IF This, Then That" (IFTTT), and lighting controls that use these rules may be referred to as the IFTTT light control. Even though the IFTTT is believed to be a smart way to control light, it is still an even triggered "reactive" type of control. A predictive system is need that is responsive to the light system user's needs and actions, as well as environmental factors, e.g., weather, date and time.

In some embodiments, the systems, methods and computer program products provide light controls that can employ a remote, e.g., cloud based, predictive computing system that employs data from the user's action with respect to lighting controls and using the data from the user's action "predictively" provides best lighting characteristic settings to a local controller for the lighting system to actuate light emissions from the lighting emitting devices, e.g., light emitting device including at least one light emitting diode (LED). The methods, systems and computer program products of the present disclosure can reduce frequency of user adjustment in lighting control systems. In some embodiments, lighting science based setting optimization improves light experience that is hard to achieve by the normal user alone. In some embodiments, the methods, systems and computer program products of the present disclosure provide for an optimized balance of energy savings and light quality.

The methods, systems and computer program products are now discussed with reference to FIGS. 1-11.

FIG. 1 illustrates an exemplary predictive lighting system 100 for a predictive lighting control that is responsive to data indicative of user actions. The lighting system includes a remote computing system for receiving lighting data based on user actions and in response to the lighting data provides a predictive lighting setting. As will be described throughout, the remote computing systems may include a machine learning device 80 and a cloud computing environment 75. In some embodiments, a local controller 20 that receives the predictive lighting setting for actuating light emitting devices 50 to emit light having the characteristics of the predictive light setting.

Figure 2:
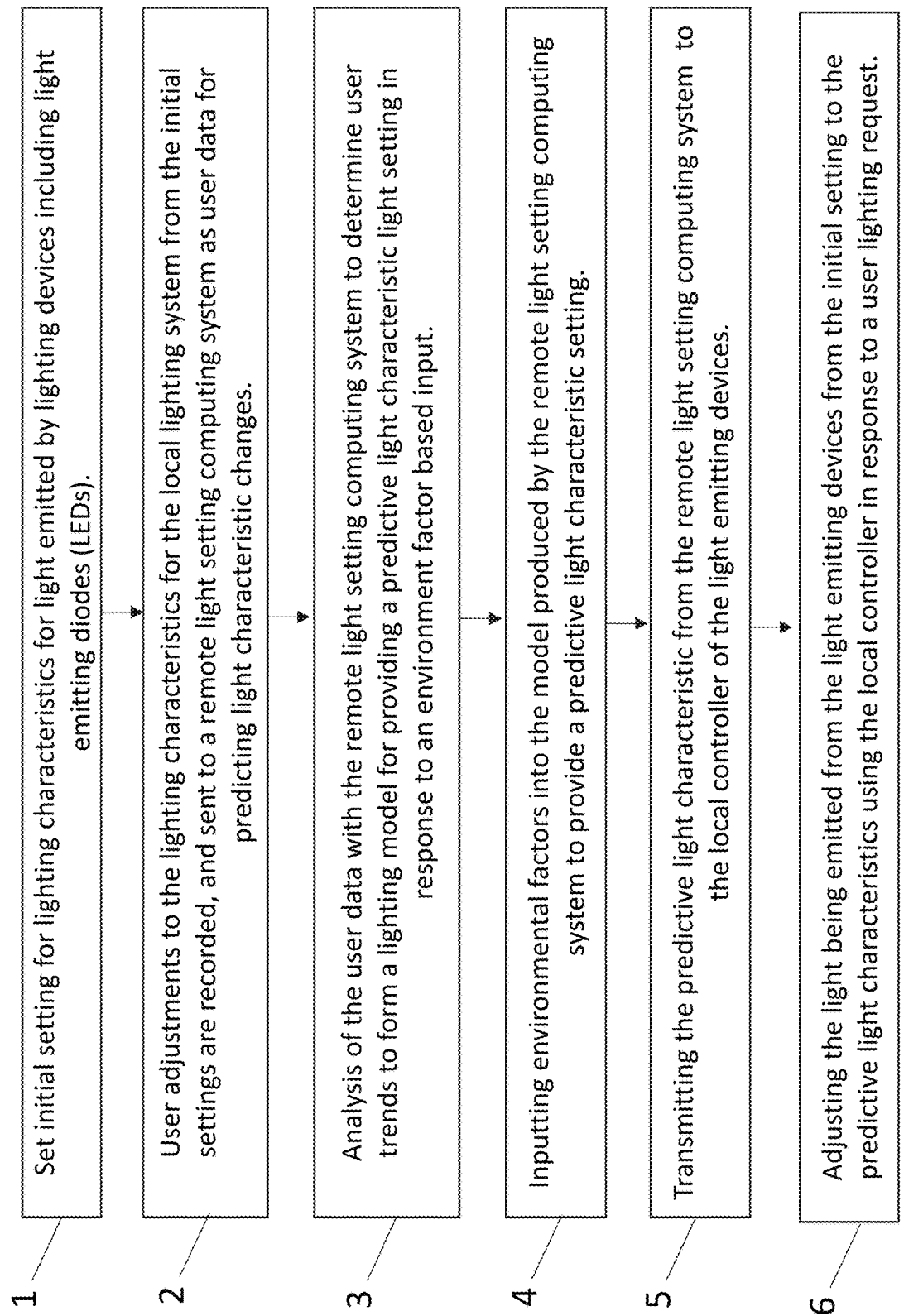
FIG. 2 is a block diagram illustrating a process flow for a method of controlling lighting characteristics of light being emitted from devices having at least one light emitting diode, the method including a remote computing system for receiving lighting data based on user actions and in response to the lighting data provides a predictive lighting setting for actuating light emitting devices to emit light having the characteristics of the predictive light setting, in accordance with one embodiment of the present disclosure.

FIG. 2 is a block diagram illustrating a process flow for a method of controlling lighting characteristics of light being emitted from devices 50 having at least one light emitting diode, the method including a remote computing system for receiving lighting data based on user actions, and in response to the lighting data provides a predictive lighting characteristic setting for actuating light emitting devices to emit light having the characteristics of the predictive light setting.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, hardware processor device or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium, e.g., physical memory, that can direct a computer, a programmable data processing apparatus, hardware processor device and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some embodiments, the module may be in the form of stored memory, and the logical function(s) can be actuated by a hardware processor device. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring to FIG. 1, in some embodiments, the systems, methods and computer program products of the present disclosure can provide a light control system 100 that includes a light emitting device 50 that includes at least one light emitting diode (LED), a local controller 20, a user terminal 40, and remote computing system (including a cloud environment 75 and a machine learning device 80) that first collects and analyzes both control, e.g., lighting characteristics in response to user activities, e.g., user enter commands, and environmental data, e.g., time, season, weather etc., and then predicts the best setting for lighting characteristics. Following the prediction of the best setting for lighting characteristics, the remote computing system sends the prediction to the local controller 20. The local controller 20 can then adjust the light emitted by the light emitting device 50 including the at least one light emitting diode (LED) to match the best control setting for lighting characteristics, i.e., predictive light characteristic setting, that was predicted by the remote computing system.

In some embodiments, the methods, systems and computer program products of the present disclosure are for controlling the lighting characteristics of lighting devices that include light emitting diodes (LEDs). A light emitting diode (LED) is a form of solid state light emitter. The term "solid state" refers to light emitted by solid-state electroluminescence, as opposed to incandescent bulbs (which use thermal radiation) or fluorescent tubes, which use a low pressure Hg discharge. In a broad sense, a light emitting diode (LED) is a semiconductor device that emits visible light when an electric current passes through it. Some examples of solid state light emitters that are suitable for the methods and structures described herein include inorganic semiconductor light-emitting diodes (LEDs), organic light-emitting diodes (OLED), polymer light-emitting diodes (PLED), surface mount light emitting diodes (SMT LEDs) or combinations thereof.

Referring to FIG. 2, in some embodiments, the method of predictive smart light controls may begin at block 1 with programming an initial setting for lighting characteristics for light emitted by lighting devices including light emitting diodes (LEDs). The initial setting may take into account the time periods of lighting, the seasons during which the light system is operated, and the different types of tasks that a user may be performing during a lighting cycle, e.g., reading, drafting, cooking, sleeping, watching video media, etc. The initial setting may also take into account a scene. A scene may be a room type, e.g., bedroom, kitchen, living room, office, etc.

In some embodiments, the method of predictive smart light controls can begin with programming an initial setting for lighting characteristics for light emitted by lighting devices including light emitted diodes (LEDs) may employ an application that is run off of a mobile computing device, which can provide the user terminal 40. The mobile computing device can be a machine for computing calculations including a hardware processor device, e.g., transistor including device, that can be a hand held device. One example of mobile computing device that is suitable for use with the light control methods, systems and computer program products that are described herein includes a phone having a touchscreen interface and an operating system capable of running applications, which can be referred to as a smart phone. In addition to cellular access, the smart phones can also have internet access. Another example of a mobile computing device that is suitable for use with the methods, systems and computer program products described herein can be a tablet computer. In some examples, the tablet computer may be a computer contained in a touchscreen panel housing. The tablet computer may have at least one of internet or cellular access. In some embodiments, the mobile computing device may be a dedicated light controller having a touch screen.

A touch screen is a display screen that is also an input device, i.e., input device to a user terminal 40. The screens are sensitive to pressure. One mechanism by which the user interacts with graphic user interface of the mobile computing device is through the touch screen by touching pictures, icons, words or any selectable image/feature that is displayed on the screen. The touchscreen may be provided by a resistive touchscreen, a surface acoustic wave touchscreen, a capacitive touchscreen or a combination thereof. Any screen that can display the graphic user interface and receiving commands through touch gestures, e.g., finger touch or stylus touch, is suitable for use with the methods, systems and computer program products described herein. As noted above, the touch screen is only one input device used in the mobile computing device for controlling lighting.

The graphical user interface (GUI) is a type of user interface that allows users to interact with electronic devices, such as the mobile computing device and luminaires, through graphical icons and visual indicators, such as secondary notation, instead of text-based user interfaces, typed command labels or text navigation.

In some embodiments, the initial setting for lighting characteristics for light emitted by lighting devices including light emitted diodes (LEDs) may include a selection from the user terminal 40 of at least one of a plurality of colors for emission of light by the light emitting device 50. The term "color" denotes a phenomenon of light or visual perception that can enable one to differentiate objects. Color may describe an aspect of the appearance of objects and light sources in terms of hue, brightness, and saturation. Some examples of colors that may be suitable for use with the method of controlling lighting in accordance with the methods, systems and computer program products described herein can include red, orange, yellow, green, blue, indigo, violet and combinations thereof, as well as the numerous shades of the aforementioned families of colors.

The color may be selected from a color wheel 15c that is displayed on the graphic user interface (GUI) of a mobile device that provides the user terminal 40. In one example of the color wheel 15c may include colors, such as red (R=red), orange (O=orange), green (G=green), blue (B=blue), indigo (I=indigo), and violet (V=violet), in which the color families are arranged following a perimeter in the ROYGBIV sequence. The color wheel 15c includes a plurality of selectable light function settings for each family of the aforementioned colors. In some embodiments, the range of lightness to darkness for each family of colors may range from the lightest colors, i.e., having a greatest degree of white, starting from the center of the color wheel (at which white (W=white) is present), in an increasing degree of darkness, i.e., having a greater degree of black, to a darkest color at the perimeter of the color wheel 15c.

In some embodiments, the initial setting for lighting characteristics for light emitted by lighting devices including light emitted diodes (LEDs) may include a selection from the user terminal 40 of a light dimming setting selection for emission of light by the light emitting device 50. In some examples, dimming or light intensity may be measured using lux. In some embodiments, the dimming or light intensity scale with selectable settings can be provided on the GUI of the mobile device that provides the user terminal 40 to provide for adjusting lighting between 100 lux to 1000 lux. For example, lighting for office work may be comfortably done at a value between 250 lux to 500 lux. For greater intensity applications, such as work areas that involve drawing or other detail work, the intensity of the lighting may be provided by luminaires that are illuminated to a range within 750 lux to 1,000 lux.

In some embodiments, the initial setting for lighting characteristics for light emitted by lighting devices including light emitted diodes (LEDs) may include a selection from the user terminal 40 of a light color temperature for emission of light by the light emitting device 50. In some embodiments, the color temperature scale including a plurality of selectable grid light functions correlated to color temperature, i.e., a measurement having the units degrees Kelvin (° K), is present on the GUI of the user terminal 40. In some examples, the range of Kelvin selected for the color temperature can range from 1K to 7K.

Figure 3:
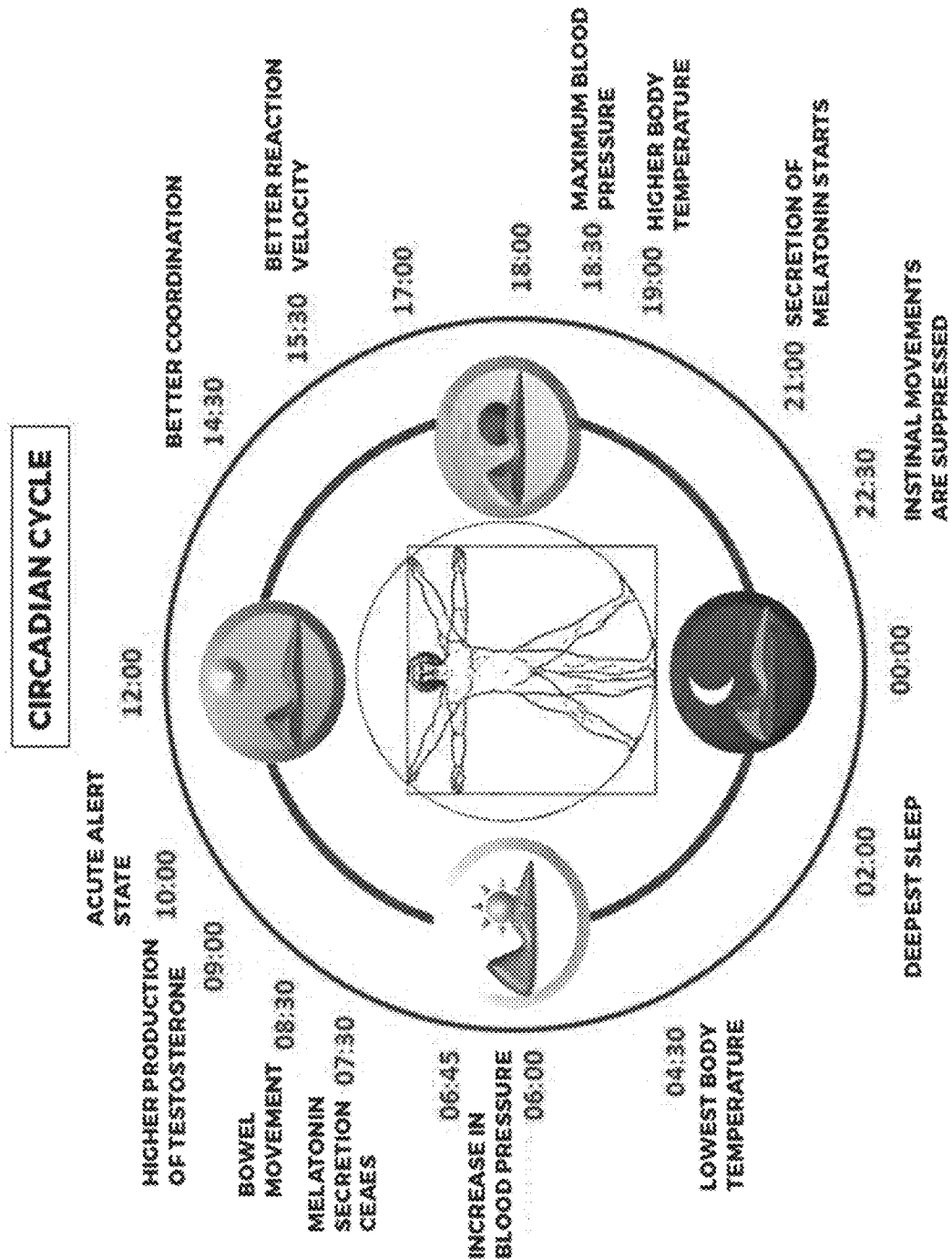
FIG. 3 is an illustration depicting human circadian rhythm, in which the depiction illustrates different human functions at time periods that are optimized for those functions, in accordance with human circadian rhythm.
Figure 4:
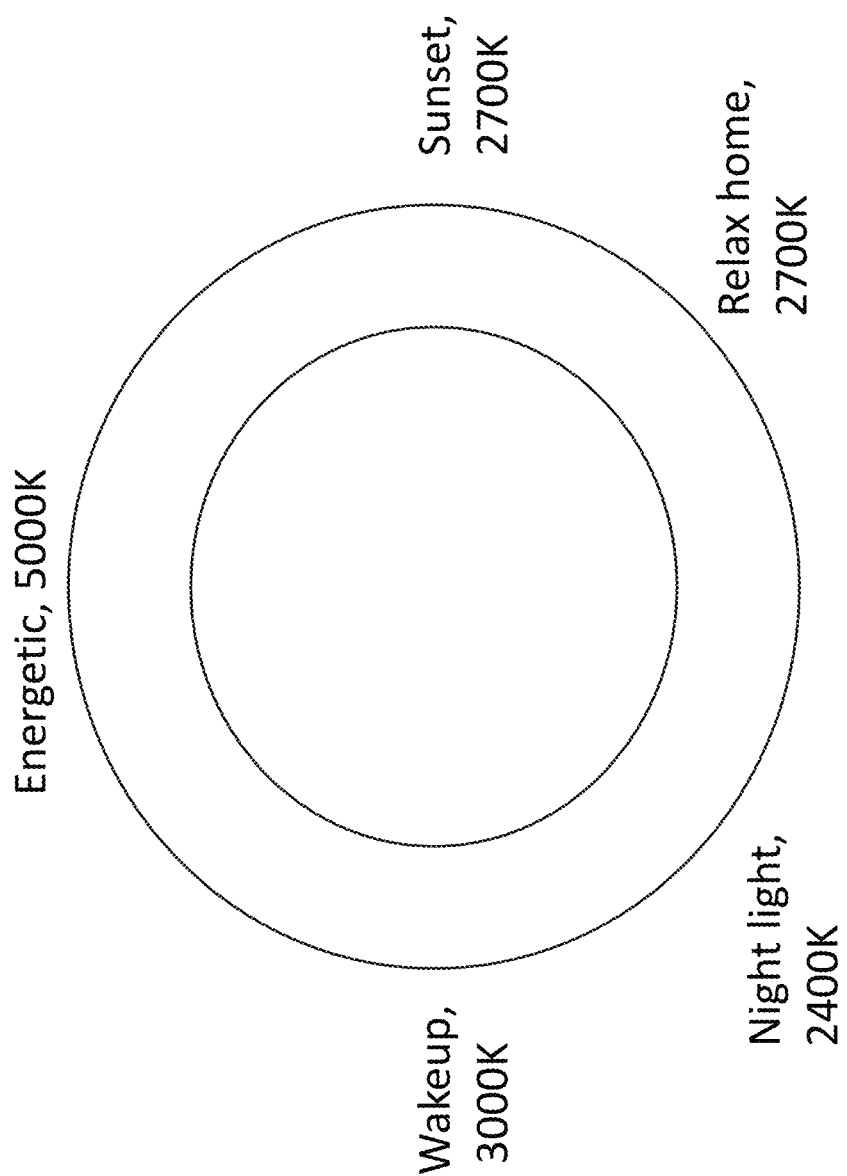
FIG. 4 is an illustration of an initial setting that correlates color temperatures in lighting to the time periods of the human circadian rhythm, in accordance with one embodiment of the present disclosure.

As noted above, the initial setting can include the selection of one of the aforementioned lighting characteristics for use in a scene setting or task setting. FIGS. 3 and 4 illustrates an exemplary embodiment of the initial setting for bedroom light, in which the lighting characteristics take into account the human circadian rhythm. Circadian rhythms are physical, mental, and behavioral changes that follow a daily cycle. They respond primarily to light and darkness in an organism's environment. Sleeping at night and being awake during the day is an example of a light-related circadian rhythm.

FIG. 3 is an illustration depicting a circadian rhythm of a human, which illustrates the different human biological functions during the hours of the day. FIG. 4 is an illustration of an initial setting that correlates color temperatures in lighting to the time periods of the human circadian rhythm. Comparison of FIGS. 3 and 4 illustrate one example of an initial set up for lighting controls in which the light color tone changes with time according to the human circadian rhythm. For example, at noon, i.e., 1200, of the circadian rhythm depiction in FIG. 3, the color temperature setting may be equal to 5000K for energetic human behavior, as depicted in FIG. 4. In another example, at approximately 18:00 of the human circadian rhythm, which may be the time of highest blood pressure and/or highest body temperature, the color temperature setting may be equal to 2700K for sunset, as depicted in FIG. 3. In another example, at approximately 21:00 of the human circadian rhythm, which may be the time at which melatonin secretion starts, the color temperature setting may be equal to 2700K for relaxation, as depicted in FIG. 3. In another example, at approximately 2:00 of the human circadian rhythm, which may be the time of deepest sleep, the color temperature setting may be equal to 2400K for a night light, as depicted in FIG. 3. In another example, at approximately 6:00 of the human circadian rhythm, the color temperature setting may be equal to 3000K for wakeup, as depicted in FIG. 3. Weather, seasonal and day time saving arrangements are also taken into account for the initial settings.

The depiction of color temperature on the circular graph corresponding to the time periods of the human circadian rhythm depicted in FIG. 4 can provide a screen shot or a user interface, i.e., GUI, on the display of the user terminal 40, in which the users set the initial settings for light characteristics settings in block 1 of FIG. 2.

The color temperatures and time periods depicted in FIG. 4 illustrate one example of light characteristic settings that can be entered into the user terminal 50 by the user for the initial settings for light characteristics of block 1 of FIG. 2.

In another embodiments, the light characteristic settings for the initial settings may be initially programmed to be time, location and season dependent. In an example for the initial setting of bedroom lighting, the default light intensity, i.e., dimming, changes with time according to at least one of the human circadian rhythm, the day time saving arrangement, sunlight and weather condition, seasonal adjustment, and combinations thereof.

Figure 5:
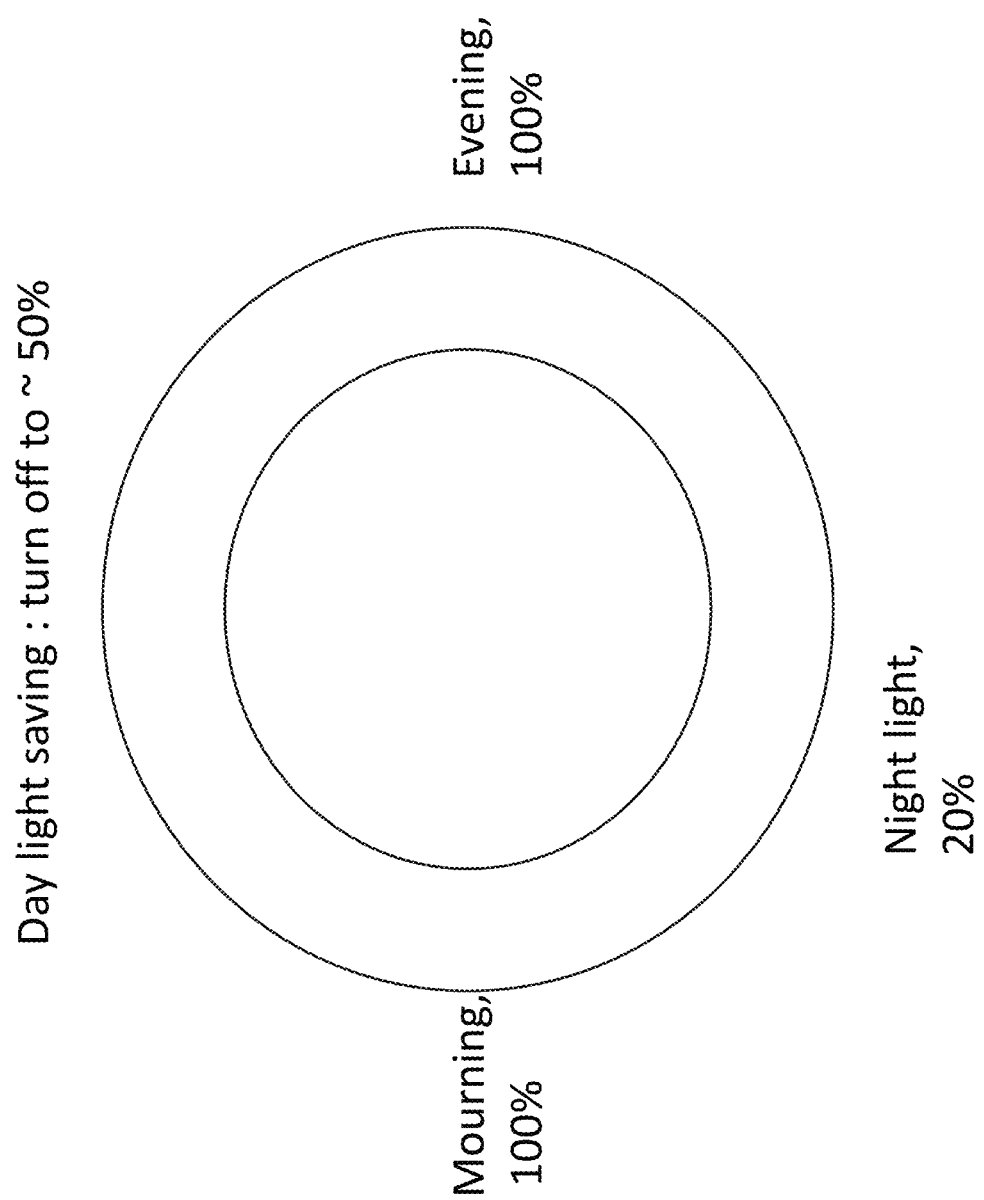
FIG. 5 is an illustration of an initial setting that correlates light intensity in lighting to the time periods of the human circadian rhythm, in accordance with one embodiment of the present disclosure.

Comparison of FIGS. 3 and 5 illustrate one example of an initial setup for lighting controls in which the light intensity changes with time according to the human circadian rhythm. For example, the default light intensity can be reduced to half during the daytime when natural light is strong. This is depicted as "day light saving: turn off to ~50% full power" in FIG. 5, which corresponds to range ending from 10:00 for "high alertness" to 14:30 for "best coordination", in which 12:00 represents noon, as illustrated on the human circadian rhythm plot depicted in FIG. 3. In some examples, if the weather forecast is overcast or rain, the default light intensity is increased up to full brightness, i.e., 100%. Full bright (i.e., 100% in FIG. 5) in the morning and evening may be the light setting for the light emitted by the light emitting devices 50 when natural light is insufficient or not available. In some examples, the default light intensity is reduced to night mode (~20%) to reduce the light shock effects when light is turn on at deep night. This portion of the graph depicted in FIG. 5 correlates to 2:00 of the human circadian rhythm plot depicted in FIG. 3 that is referred to as "deepest sleep".

The depiction of color intensity on the circular graph corresponding to the time periods of the human circadian rhythm depicted in FIG. 5 can provide a screen shot or a user interface, i.e., GUI, on the display of the user terminal 40, in which the users set the initial settings for light characteristics settings in block 1 of FIG. 2.

Figure 6:
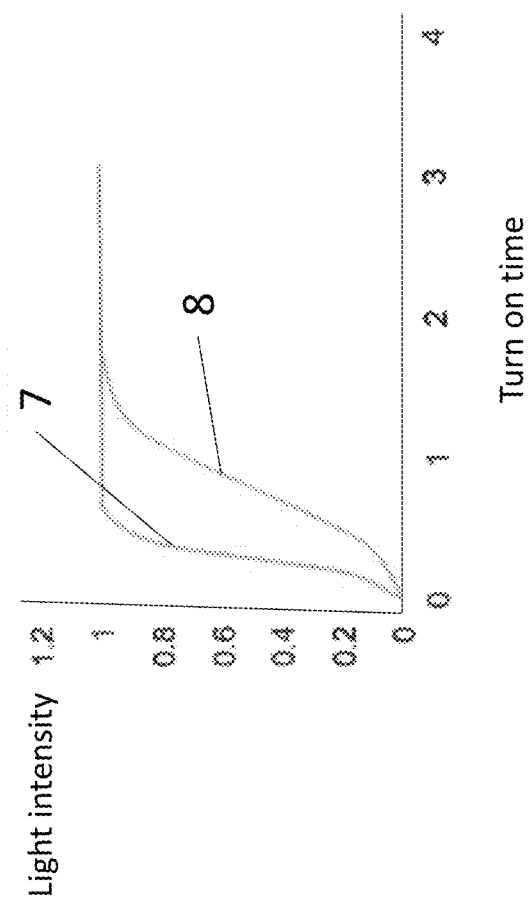
FIG. 6 is a plot illustrating a substantially instant transition from OFF to ON and ON to OFF for a lighting device in comparison with a moderate transition from OFF to ON and ON to OFF in a lighting transition.

In addition to color temperature and intensity, the initial set up for lighting controls at block 1 of FIG. 2 may further include default OFF-ON and ON-OFF transitions. In one exemplary embodiments, for a bedroom light initial setting, the default OFF-ON and ON-OFF transition changes with time. The default OFF-ON and ON-OFF transition time for day time light is instant on and off. Default transition from OFF to ON and ON to OFF at night can be gradually increased. FIG. 6 is a plot illustrating a substantially instant transition from OFF to ON and ON to OFF that is identified by reference number 7 in comparison with a moderate transition from OFF to ON and ON to OFF that is identified by reference number 8. In some examples, the default OFF-ON and ON-OFF transition time from morning and evening is moderate.

In some embodiments, the default initial set up for lighting controls includes default ON, OFF and dim down settings. In one exemplary embodiment, the bedroom light initial settings, the default ON, OFF and dim down settings take day time savings into account automatically, the light automatically dim down after 11 pm, and automatically turn on to full bright at 6:30 AM. Unless, overridden by user, the default state of light will be off during "business hours" on week days. The default on an off schedule will be adjusted either manually by end user or automatically per the end user's calendar.

It is noted that the above examples are provided for illustrative purposes only, and it is not intended that the present disclosure be limited to only these light characteristic examples. Additionally, although each of the examples include a bedroom scene, the examples are not only limited to this scene. Other scenes that can be selected may include other room types, such as bathrooms, kitchens, offices, hallways, garages, and other rooms, etc. In addition to scene selections, the method can allow for light function form selections. Examples of light function forms that can be selected can include hanging pendant lamps, table lamps, chandeliers, 2×2 and/or 2×4 tube lighting office type fixtures, desk lamps, floor standing lamps, recessed can downlights, and light sources with heat sinks, as well as any other type of similar light function forms.

The aforementioned examples of initial set ups for lighting controls can be entered to the lighting control system 100 via the user terminal 40. The user terminal 40 can be a wireless smart phone/tablet with the appropriate applications installed; or the user terminal 40 can be a computer having a wired keyboard.

Figure 7:
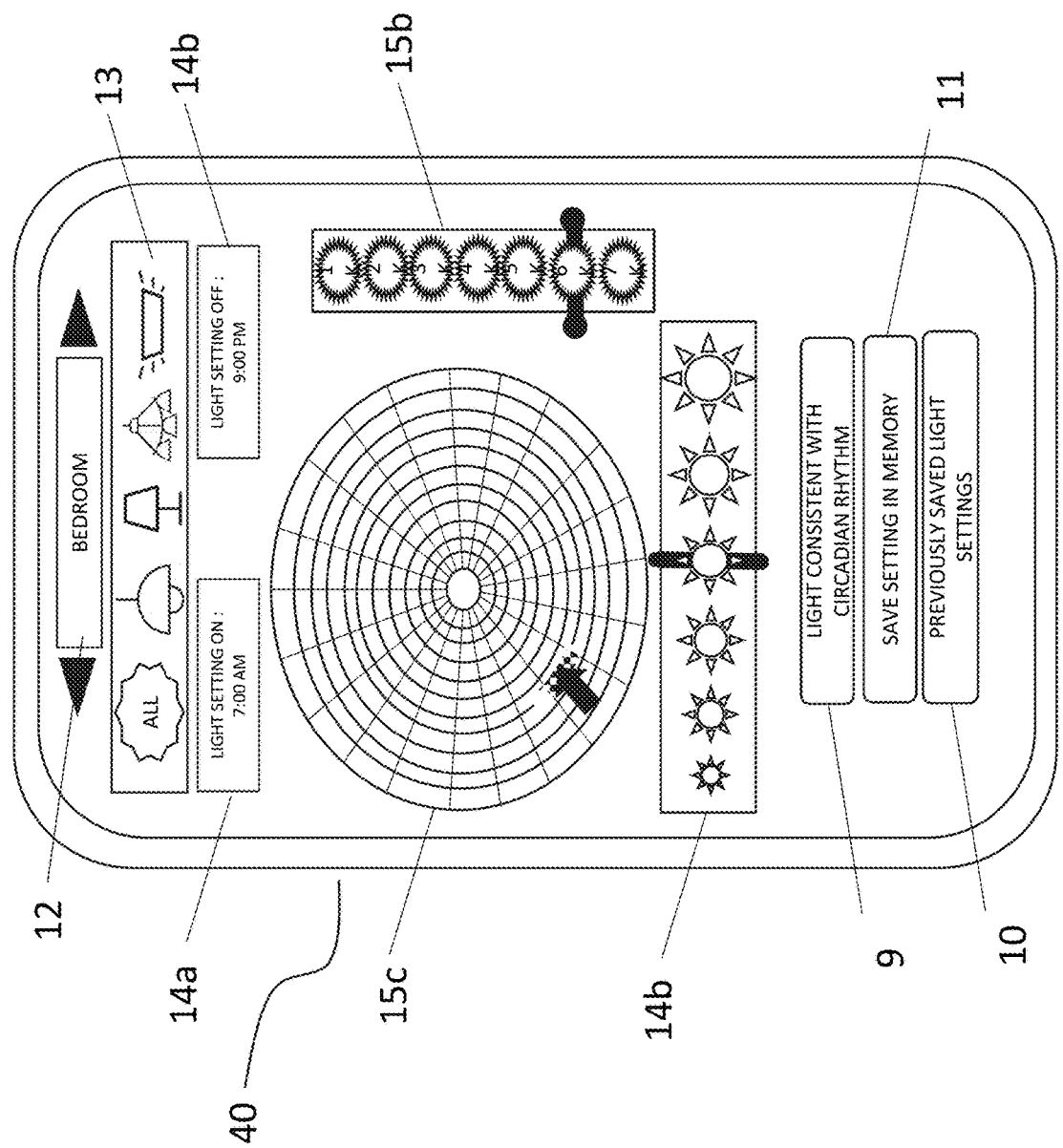
FIG. 7 is an illustration depicting a screen shot of a graphic user interface on a mobile device depicting an application for setting and adjusting light characteristics for light emitted by light emitting devices, in accordance with one embodiment of the present disclosure.

FIG. 7 illustrates one embodiment of a screen shot of a mobile device, such as a smart phones, being employed for the user terminal 40, which can be used for entering initial light characteristic settings. The screen shot may be of a graphic user interface, in which a touch screen interface may be used to select settings correlated to light characteristics to be emitted from the light emitting devices 50. For example, a first scale 15a may be provided for selecting color temperature settings, a second scale 15b may be provided for selecting light dimming/light intensity settings, and a color wheel 15c for selecting light color settings. The graphic user interface/screen shot depicted in FIG. 7 may also include a field for entering a time that a selected light characteristic setting is activated 14a, and a field for entering a time that a selected light characteristic setting id deactivated 14b. The graphic user interface/screen shot may also include a field for selecting the scene 12, e.g., bedroom, in which the lighting is being adjusted; and may also include a field for selecting the form factor 13, i.e., type of lamps, for which the lighting is being adjusted. In some embodiments, the graphic user interface/screen shot for the user interface 40 may also include a selectable field to save a setting within the memory of the system for a selected setting of light characteristics, i.e., "save setting in memory" 11, and a field to select if the user wishes to selected previously saved light settings, i.e., "previously saved light settings" 10. In some embodiments, the graphic user interface/screen shot for the user interface 40 may also include a selectable field that actuates a specific arrangement of lighting characteristics to be displayed by the light emitting devices 50, such as lighting consistent with circadian rhythm" 9.

The user terminal 40 may be in wireless communication with a local controller 20 of the light control system 100. The local controller 20 may be a device that receives, transforms, saves, executes, coordinates and transmits data among and/or between the cloud systems 75, e.g., remove predictive light setting computing system including the machine learning device 80, user terminal(s) 40, and light emitting device 50. Exemplary local controllers 20 can be light control gateway, smart wall plate, and/or smart light units, e.g., luminaires, bulbs, fixtures, etc.

Referring to FIG. 1, the local controller 20 may be in communication, i.e., wireless communication, with a remote predictive light setting computing system including a machine learning device 80 and cloud computing environment 75 for receiving lighting data based on user actions. In response to the lighting data, the remote predictive light setting computing system provides a predictive lighting setting for actuating light emitting devices 50 to emit light having the characteristics of the predictive light setting. The local controller 20 may be an independent device, or the local controller can be a component of the light emitting devices 50.

In the embodiments, in which the remote predictive light setting computing system 75, the local controller 20 and the light emitting devices 50 are separate devices interconnected wirelessly, the wireless connection may be included by any one of the following: WiFi, Bluetooth, internet based connections, cellular connections and combinations thereof. In other embodiments, the communication between the remote predictive light setting computing system 75, the local controller 20 and the light emitting devices 50 may be through a wired connection, such as a local network connection, e.g., ethernet type connection. As described in further details below, the remote predictive light setting computing system 75, the local controller 20 and the light emitting devices 50 may include communications modules providing for intercommunication between the devices.

The remote predictive light setting computing system may be a cloud based system. In some embodiments, the remote predictive light setting computing system includes a machine leaning device 80 and a cloud computing environment 75. "Cloud computing" is the practice of using a network of remote servers hosted on the Internet to store, manage, and process data, rather than a local server or a personal computer. Cloud computing is an information technology (IT) paradigm that enables ubiquitous access to shared pools of configurable system resources and higher-level services that can be rapidly provisioned with minimal management effort, often over the Internet. Cloud computing relies on sharing of resources to achieve coherence and economies of scale, similar to a public utility. The cloud service may be public cloud, private cloud or hybrid cloud.

In some embodiments, the cloud computing environment provides for a remote computing system for predictive light setting computing. As will be described in further detail below, the remote predictive light setting computer system can perform analysis of user date to form a lighting model for providing a predictive light characteristic light setting in response to an environment factor based input. This is block 3 of FIG. 2. The user data that is used by the remote predictive light setting computer system may include adjustments to the light characteristics of light being emitted by the light emitting devices 50 that deviates from the initial setting for light characteristics for light emitted by the light emitting devices 50 that is configured in block 1 of FIG. 2. The adjustments can be changes to color of the light emitted by the light emitting devices 50; changes to the color temperature of the light emitted by the light emitting devices 50; changes to the light intensity/dimming of the light emitted by the light emitting devices 50; and/or changes to the "ON"/"OFF" switching behavior of the light emitting devices 50. It is further noted that timing, e.g., what hour of the day/night, of the changes to the lighting characteristics is also considered in measuring the adjustments to the light characteristics of the light being emitted by the light emitted devices 50, which is included in the user data.

Referring to FIG. 2, because the user adjustments are used by the remote light setting computing system to provide a lighting model for predicting light characteristic changes, the method of the present disclosure may include a step of user adjustments to the lighting characteristics for the local lighting system from the initial settings being recorded at block 2. Block 2 further includes sending the recorded adjustments to the lighting characteristics to the remote light setting computing system 75, in which the recorded adjustments may be referred to as user data for predicting light characteristic changes.

In some embodiments, the adjustments to the light characteristics in the local lighting system are recorded by the local controller 20 that is synchronized with the light emitting devices 50 that are being adjusted by the users. The adjustments can be manually made by the users. For example, the local controller 20 may be in communication, e.g., wireless communication, with the light emitting devices 50; and the local controller 20 may have the capability to allow a user to modify the lighting characteristics of the light emitting devices 50, e.g., by manually selecting via a keypad on the local controller 20 the lighting characteristics of light emitted by the light emitting devices 50 to be adjusted. In this example, the local controller 20 through which lighting characteristics are manually being entered by the user is in communication, e.g., wireless communication, with the remote predictive light setting computing system 75, in addition to being in communication with the lighting emitting devices 50.

Figure 8:
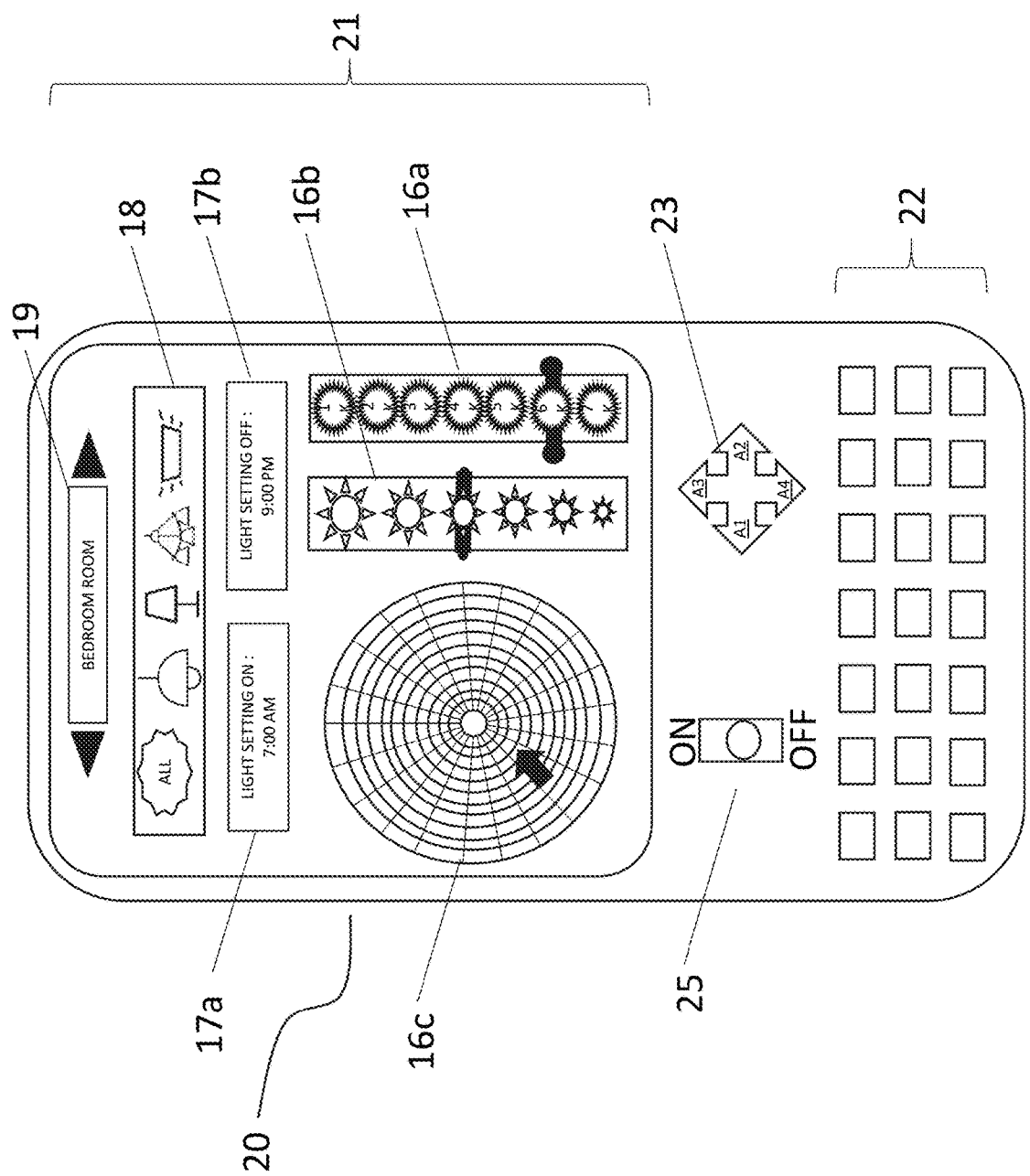
FIG. 8 is a perspective view of the interface of a local controller for adjusting light characteristics for light emitted by light emitting devices, in accordance with one embodiment of the present disclosure.

FIG. 8 illustrates one example of the interface of a local controller 20 through which a user may enter adjustments to the lighting characteristics of the light being emitted by the light emitting device 50. The interface of the local controller 20 can include a display screen 21 for displaying selectable light characteristics for entering user adjustments to the light. For example, the display screen 21 can display a first scale 16a may be provided for selecting color temperature settings, a second scale 16b may be provided for selecting light dimming/light intensity settings, and a color wheel 16c for selecting light color settings. The display screen 21 of the local controller 20 depicted in FIG. 8 may also include a field for entering a time that a selected light characteristic setting is activated 17a, and a field for entering a time that a selected light characteristic setting id deactivated 17b. The display screen 21 may also include a field for selecting the scene 19, e.g., bedroom, in which the lighting is being adjusted; and may also include a field for selecting the form factor 18, i.e., type of lamps, for which the lighting is being adjusted.

Referring to FIG. 8, the user interface to the local controller 20 may include a keypad 22 for entering information regarding adjustments to the light characteristics of the light being emitted by the light emitting devices 50. In some embodiments, the user interface includes a plurality of arrows for traversing a cursor on the displayer 21 for selecting selectable light settings that being displayed on the display of the local controller 20. It is noted that the display itself may also be a touch screen display providing further means for users to interface with the local controller in selecting light settings from those being displayed on the local controller display 21.

Referring to FIG. 8, the local controller 20 can have the geometry for a wall mount interface similar to dimmer controls and on/off switches. In some examples, the local controller 20 can include a rocker switch 25, in which activation of the rocker switch may can turn the light emitting devices 50 from ON to OFF, and vice versa. A user switching the rocker switch 25 to the ON position illuminates the light emitting devices 50 with the predictive light characteristic light setting, as described herein.

The user does not necessarily have to enter the adjustments to the light characteristics of the light being emitted by the light emitting devices 50 through the local controller 20. For example, an application on the user interface 40, such as the application that the user employed to enter the initial setting for lighting characteristics for light emitted by lighting devices, may be employed to enter adjustments to the lighting characteristics, in which commands for adjustments to the lighting characteristics are sent from the user interface to the local controller 20. In this instance, the user interface 40 may be provided by a smart phone, tablet, laptop and/or desktop computer. In other embodiments, the application through which commands for adjustments to the lighting characteristics are sent to the local controller 20 is integrated into the light emitting devices 50 themselves or is integrated into a separate device that controls the light emitting devices 50, e.g., an alarm clock application that in addition to functioning as an alarm clock controls lighting to correspond with the wake up alarm.

The local controller 20 records the adjustments to the light characteristics for the light emitted by the light emitting devices 50, and then sends the adjustments to the remote light setting computing system, i.e., to the machine learning device 80 over the cloud computing environment 75, as user data at block 2 of FIG. 2.

Referring to FIG. 2, in a following step at block 3, the method for providing predictive lighting control can continue with the analysis of the user data with the remote light setting computing system to determine user trends to form a lighting model for providing a predictive light characteristic light setting in response to an environment factor based input. As will be described in the following examples, the adjustments to the lightings characteristics can include user adjustments, such as calendar based automatic adjustment and/or end user manual adjustments; user adjustment data analysis based upon light levels and weather; light control optimization; and on demand predictive medicine. These lighting adjustments are considered in view of the initial lighting characteristics for the light emitted by the light emitting devices which are based upon the human circadian rhythm. In view of light profile that is consistent with the human circadian rhythm and the user adjustments to the light characteristics for the light emitted from the light emitting devices 50, the remote predictive light setting computing system 75 using machine learning produces a model for providing predictive light characteristics in response to environmental inputs, such as time, weather and calendar date.

Machine learning employs statistical techniques to give computer systems the ability to "learn" (e.g., progressively improve performance on a specific task) with data, without being explicitly programmed. The machine learning method that can be used to form the lighting model for providing the light characteristic light setting in response to an environment factor based input can include decision tree learning, association rule learning, artificial neural networks, deep learning, inductive logic programming, support vector machines, clustering analysis, bayesian networks, reinforcement learning, representation learning, similarity and metric learning, sparse dictionary learning, genetic algorithms, rule-based machine learning, learning classifier systems, and combinations thereof. The remote predictive light setting computing system using machine learning produces a model for providing predictive light characteristics in response to environmental inputs, such as time, weather and calendar date may include a machine learning algorithm that can be selected from the group consisting of: Almeida-Pineda recurrent backpropagation, ALOPEX, backpropagation, bootstrap aggregating, CN2 algorithm, constructing skill trees, dehaene-changeux model, diffusion map, dominance-based rough set approach, dynamic time warping, error-driven learning, evolutionary multimodal optimization, expectation-maximization algorithm, fastICA, forward-backward algorithm, geneRec, genetic algorithm for rule set production, growing self-organizing map, HEXQ, hyper basis function network, IDistance, K-nearest neighbors algorithm, kernel methods for vector output, kernel principal component analysis, leabra, Linde-Buzo-Gray algorithm, local outlier factor, logic learning machine, LogitBoost, manifold alignment, minimum redundancy feature selection, mixture of experts, multiple kernel learning, non-negative matrix factorization, online machine learning, out-of-bag error, prefrontal cortex basal ganglia working memory, PVLV, Q-learning, quadratic unconstrained binary optimization, query-level feature, quickprop, radial basis function network, randomized weighted majority algorithm, reinforcement learning, repeated incremental pruning to produce error reduction (RIPPER), Rprop, rule-based machine learning, skill chaining, sparse PCA, state-action-reward-state-action, stochastic gradient descent, structured kNN, T-distributed stochastic neighbor embedding, temporal difference learning, wake-sleep algorithm, weighted majority algorithm (machine learning) and combinations thereof.

It is noted that a machine learning device 80 may be employed to employ one of the aforementioned machine learning methods and/or machine learning algorithms in providing the model for providing predictive light characteristics in response to environmental inputs, such as time, weather and calendar date. The machine learning device 80 typically includes at least one form of physical memory for storing instructions for executing a machine learning process using at least one hardware processor for providing the model for providing predictive light characteristics in response to environmental inputs. The machine learning device 80 is at a remote location, i.e., separate location, from the local controller 20. The machine learning device 80 may be in communication with the local controller 20 through a could computing environment 75 that provides the remote predictive light computing system where the user adjustment data is analyzed with other parameters to provide a predictive light characteristic setting.

Referring to FIG. 2, in a following step, the lighting methods may continue with inputting environmental factors into the model produced by the remote light setting computing system to provide a predictive light characteristic setting. The environmental factors may include time, calendar date, and weather. In this case the calendar date provides an environmental factor due to the changes in the sunset and the sunrise and the number of daylight hours in a day.

In one example of the method steps described with reference to blocks 2, 3 and 4 of FIG. 2, user adjustments to the lighting characteristics for the local lighting system from the initial settings may be selected to change the lighting within a bedroom scene, wherein the adjustment may be a calendar based automatic adjustment. For example, if the controller of a bedroom light is synchronized with an end user's wakeup alarm application or from an end user's calendar, in which the light will gradually light up and blink for a few seconds either simultaneously with the wakeup alarm, or act alone at the user's choice. End users can adjust, i.e., manually adjust, the light control settings, e.g., the lighting control settings employed during the users wakeup alarm application, manually via a key pad attached (if any), e.g., the manual interface to the local controller 20 or an interface of a separate device controlling the light emitting devices, or via an application being run on a smart phone, tablet, or desktop computer, e.g., user interface 40. The user adjustment data, i.e., changes to lighting characteristics entered by the user, as well as date and time and other environmental factors for when the user adjustments were executed, can then be sent to the remote light computing system. Not like prior lighting controls, where user adjustment data is saved and used continually till the next user adjustment; in this example, the user adjustment data is transmitted to the remote predictive light computing system where the user adjustment data is analyzed with other parameters to provide a predictive light characteristic setting. More specifically, the calendar based changes in lighting, the manual adjustments, and the interactions between the wakeup alarm application and the light emitting devices 50 can provide the light adjustments for blocks 2 and 3 of the method depicted in FIG. 2.

In another example, adjustments to the lighting characteristics for the local lighting system from the initial settings may be selected to change the lighting within a bedroom scene, wherein the adjustments may be a predictive adjustment taking into account weather, calendar dates and time. Light setting adjustments can be entered into the predictive light control system 100 through the local controller 20, or an application for making light setting adjustments on a user interface 40, which can be provided by a smart phone, tablet and/or desktop computer. The calendar settings can be entered into the predictive light control system 100 via a calendar application run on a user's device, such as a smart phone, tablet, or desktop computer, e.g., user interface 40. Weather data can be entered into the predictive light control system 100 via a weather application run on a user's device, such as a smart phone, tablet, or desktop computer, e.g., user interface 40; or a remote weather reporting service that connects to the predictive light control system 100 through the cloud computing environment 75 that communicates with the remote predictive light computing system, e.g., machine learning device 80.

In one example, if a user adjusted the light to a higher level during a sun filled day time, a future day time level will be kept to that higher level. Contrarily, if that same adjustment is made only on rainy days, that adjustment to higher levels of lighting is only applied on rainy days. This is an example of lighting controls that are responsive to user adjustment data analysis. The light adjustments in response to sun filled days and rainy days can provide the light adjustments for blocks 2 and 3 of the method depicted in FIG. 2.

In one example, the lighting control system may include a light control optimization feature. In one example of a light control optimization feature, if there is an early morning event, the light may dim down the number of hours that a user wishes to sleep ahead of the morning event, wherein when the light first dims reminds the user to go to bed early. For example, if there is an early morning event, the light may dim down 8 hours ahead of the even to remind the user to go to bed early. The light adjustments in response to scheduled events having specific lighting needs, i.e., an optimization feature type event, can provide the light adjustments for blocks 2 and 3 of the method depicted in FIG. 2.

Predictive and/or optimized light control data is sent to the local controller 20 on a regular basis, e.g., daily. The local controller 20 can then save the data, and executes the predictive or optimized data accordingly.

In another example, adjustments to the lighting characteristics for the local lighting system from the initial settings may be selected to change the lighting within a bedroom scene, wherein the adjustments may be an on demand prescription. Light setting adjustments for the on demand prescription can be entered into the predictive light control system 100 through the local controller 20, or an application for making light setting adjustments on a user interface 40, which can be provided by a smart phone, tablet and/or desktop computer. However, the settings for an on demand prescription may also be loaded directly into the predictive lighting control system 100 through the cloud computing environment that is in communication with the remote predictive light computing system.

In one example, the demand prescription may include jet lag adjustment lighting. By employing predictive light control, jet lag adjustment lighting can be delivered a few days ahead of a trip, during the trip, and after the trip. The prescribed light setting for each state of the jet lag treatment, i.e., days ahead of trip, during the trip and after the trip, may each have different lighting characteristics for the light emitted by the light emitted devices 50.

In another example, the demand prescription may include lighting characteristic adjustments to compensate for seasonal affective disorder (SAD). SAD is a type of mood disorder that triggers symptoms of depression or bipolar disorder, most often in the fall and winter when there's less sunlight. In some embodiments, the demand prescription increases the amount of lighting to offset SAD.

The light adjustments in response to lighting requirements of an on-demand prescription can provide the light adjustments for blocks 2 and 3 of the method depicted in FIG. 2.

As described above, at block 4 of the method described in FIG. 2, the method may include inputting environmental factors into the model produced by the remote light setting computing system to provide a predictive light characteristic setting. As noted above, the environmental factors take into account changes in lighting that result from weather, i.e., sun vs. rain vs. cloud, time, i.e., time periods of low light and time period of maximum light, etc.; and calendar date, i.e., seasonal changes in lighting. Other environmental factors may be the level of light that is measured by the local controller 20. For example, at least one light sensing sensor 41 may be in communication with the local controller 20. By providing initial light characteristic settings optimized to the human circadian rhythm, measuring the light adjustments made by specific users, and providing a model from those light adjustments that provides predictive light characteristics in response to environmental factors; the methods provided herein produce lighting optimized to the needs of specific users.

Referring to FIG. 2, the method may continue with transmitting the predictive light characteristic from the remote light setting computing system, e.g., the combination of the cloud computing environment 75 and the machine learning device 80, to the local controller 20 of the light emitting devices 50 at block 5. As noted above, the remote light setting computer system is in wireless communication with the local controller 20. The local controller 20 is also in wireless communication with the light emitted device 50. The predictive light characteristics that are based on time, day time saving, and weather etc. are saved at the local controller 20. The predictive light characteristics produced by the remote light setting computing system, and saved in the local controller 20, provides optimized control data for the light emitted by the light emitting device.

Referring to FIG. 2, the method may further include at block 6 adjusting the light being emitted from the light emitting devices 50 from the initial setting to the predictive light characteristics using the local controller 20. The optimized control data for the light emitted by the light emitting device provided by the predictive light characteristics that are saved on the local controller 20 is sent to the light emitting devices 50 in response to a user's actions to adjust a lighting device, or in response to a device under the control of the user to adjust a lighting device. The optimized control data is sent to the light emitting device 50 to illuminate or change the settings of light characteristics for light being emitted by the light emitting device 50. This step is typically performed after the lighting model for providing a predictive light characteristic light setting in response to an environment factor based input at blocks 3 and 4. More specifically, when a user adjusts lighting characteristics, the predictive light control system 100 considers the type of adjustment, and calculates the lighting model with an environmental input contemporary to the time of the light adjustment to provide the predictive lighting characteristic. Following transmission to the controller 20 from the remote light setting computer system at block 5, the local controller 20 sends a command to the light emitting devices 50 to reconfigure the light being emitted from the light emitting devices 50 from the initial characteristics to the predictive light characteristic setting, which takes into account user adjustments as well as environmental impact.

It is noted that the user's actions to adjust a lighting device, or the actions of the device under the control of the user to adjust a lighting device, in addition for calling for lighting of the light emitting devices with the predictive lighting characteristic settings at block 6 of FIG. 2, the user actions/device actions are also an adjustments to the lighting characteristics for the local lighting system that are sent to the remote light setting computing system, e.g., machine learning device 80 via the cloud computing environment 75, as user data for predicting light characteristic changes at block 2 of the method depicted in FIG. 2. This provides for continued analysis of the user's lighting performance requirements by the machine learning device 80, and the continued development of the lighting model for providing a predictive light characteristic light setting in response to an environment factor based input.

In another aspect of the present disclosure, a system is provided for controlling lighting using predictive light characteristics. Referring to FIG. 1, in one embodiment, the system may include a local controller 20 for sending commands to control light emissions from at least one light emitting device 50, and for recording user adjustments to the lighting characteristics of the light emissions from the at least one light emitting device 50 from an initial setting as user data. The system for controlling lighting may also include a remote light setting computing device, i.e., machine learning device 80 and cloud computing environment 75, for analyzing the user data received from the local controller 20. In some embodiments, the remote light setting computing device analyzes the user data to provide a lighting model for providing a predictive light characteristic light setting in response to an environment factor based input. The remote light setting computing device 75 transmits the predictive light characteristic light setting to the local controller 20 for commands to control light emissions from the at least one light emitting device.

Still referring to FIG. 1, the system can further include an application run on a mobile device as a user interface 40 for entering the initial setting for the lighting characteristics of light emissions from the at least one light emitting device 50. The application that is run on the mobile device may also provide a user interface 40 for entering user adjustments to the lighting characteristics of the light emissions from the at least one light emitting device 50.

Referring to FIG. 1, the remote light setting computing device includes a machine learning device 80 in communication with the local controller 20 using a cloud computing environment 75, wherein the machine learning device 80 employs a leaning method to provide the lighting model for providing a predictive light characteristic light setting, the learning method selected from the group consisting of decision tree learning, association rule learning, artificial neural networks, deep learning, inductive logic programming, support vector machines, clustering analysis, bayesian networks, reinforcement learning, representation learning, similarity and metric learning, sparse dictionary learning, genetic algorithms, rule-based machine learning, learning classifier systems, and combinations thereof.

Figure 9:
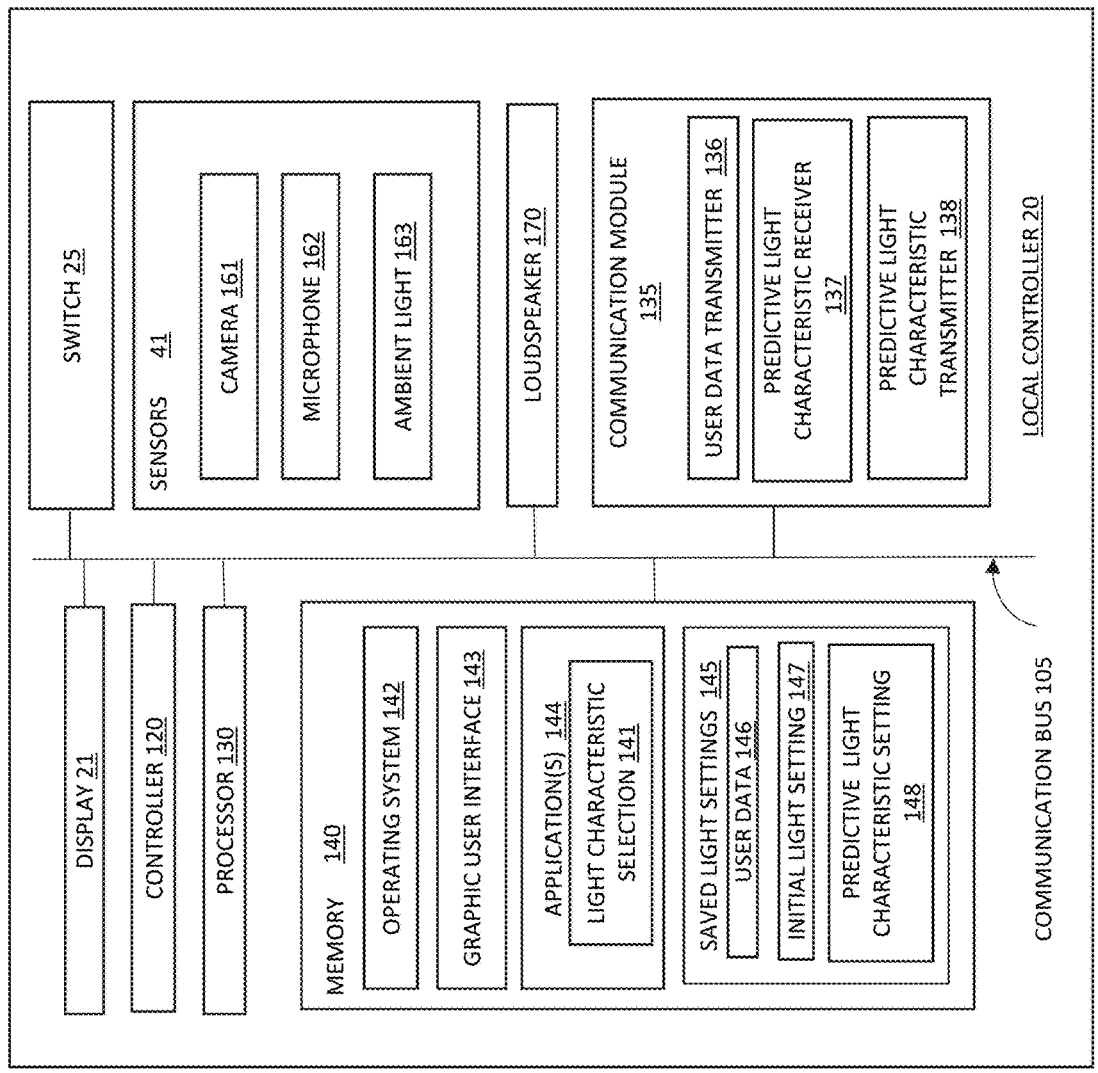
FIG. 9 is an illustration (block diagram) an exemplary local controller for interfacing with the system for controlling lighting using predictive light characteristics, in accordance with an embodiment of the present disclosure.

Referring to FIGS. 1, 8 and 9, the local controller 20 may include an interface for entering at least one of the initial setting for the lighting characteristics of light emissions from at least one light emitting device 50, and entering said user adjustments to the lighting characteristics of said light emissions from said at least one light emitting device 50. Referring to FIGS. 8 and 9, the interface may include the graphic user interface 143, the display 21, the key pad 22 and the arrow key controls 23.

The display 21 can be any electronic visual display or other device configured to display or otherwise generate an image (e.g., image, video, text, and/or other displayable content) therefrom. In some embodiments, the display 21 is a touchscreen display or other touch-sensitive display that can utilize any of a wide range of touch-sensing techniques, such as, for example: resistive touch-sensing; capacitive touch-sensing; surface acoustic wave (SAW) touch-sensing; infrared (IR) touch-sensing; optical imaging touch-sensing; and/or a combination of any one or more thereof. The touch screen display may be configured to detect or otherwise sense direct and/or proximate contact from a user's finger, stylus, or other suitable implement (which can be collectively referred to as a touch gesture) at a given location of that display 21. The touch screen display 21 may be configured to translate such contact into an electronic signal that can be processed by local controller (e.g., by the one or more processors 130 thereof) and manipulated or otherwise used to trigger a given GUI action.

Further details regarding the graphic user interface 143 that is depicted on the display 21 been provided in the above description of FIG. 8, in which the graphic user interface includes at least one of a color wheel 16c, dimming scale 16b and color temperature scale 16a.

Referring to FIG. 8, the user interface of the local controller 20 may also include a keypad 22 for said entering at least one of the initial setting for the lighting characteristics to be emitted by the light emitting devices 50, and at least one user adjustment to the lighting characteristic of light to be emitted by the light emitting devices 50. The local controller 20 can also a rocker switch for an ON and OFF light switch for the light emitting devices 50.

Referring to FIG. 9, the local controller 20 may include a communications module 135 for providing wireless communication from the local controller 20 to the remote light setting computing device, e.g., machine learning device 80, for receipt of predictive light characteristic light settings, and sending user adjustments to the remote light setting computing device, wherein the communications module 135 also provide wireless communication to the light emitting devices 50. In one example, the communications module 135 includes a transmitter, i.e., user data transmitter 136, for sending signals including data on lighting adjustments, i.e., user data, from the local controller 20 to the remote light setting computing device, e.g., machine learning device 80. In one example, the communications module 135 includes a receiver, i.e., predictive light characteristic receiver 137, for receiving at the local controller 20 predictive light characteristic settings calculated and transmitted by the remote light setting computing device, e.g., machine learning device 80. In one example, the communications module 135 includes a transmitter, i.e., predictive light characteristic transmitter 138, for transmitting from the local controller 20 a predictive light characteristic setting to the light emitting device 50, in which the light emitting device 50 projects light having characteristics matching the predictive light characteristic setting.

The communication module 135 may be configured for wired (e.g., Universal Serial Bus or USB, Ethernet, FireWire, etc.) and/or wireless (e.g., Wi-Fi, Bluetooth, etc.) communication using any suitable wired and/or wireless transmission technologies (e.g., radio frequency, or RF, transmission; infrared, or IR, light modulation; etc.), as desired. In some embodiments, the communication module 135 may be configured for communication by cellular signal used in cellular phones, and cellular type devices. In some embodiments, communication module 135 may be configured to communicate locally and/or remotely utilizing any of a wide range of wired and/or wireless communications protocols, including, for example: (1) a digital multiplexer (DMX) interface protocol; (2) a Wi-Fi protocol; (3) a Bluetooth protocol; (4) a digital addressable lighting interface (DALI) protocol; (5) a ZigBee protocol; (6) a near field communication (NFC) protocol; (7) a local area network (LAN)-based communication protocol; (8) a cellular-based communication protocol; (9) an Internet-based communication protocol; (10) a satellite-based communication protocol; and/or (11) a combination of any one or more thereof. It should be noted, however, that the present disclosure is not so limited to only these example communications protocols, as in a more general sense, and in accordance with some embodiments, any suitable communications protocol, wired and/or wireless, standard and/or custom/proprietary, may be utilized by communication module 135, as desired for a given target application or end-use.

The local controller 20 may include memory 140 and one or more processors 130. Memory 140 can be of any suitable type (e.g., RAM and/or ROM, or other suitable memory) and size, and in some cases may be implemented with volatile memory, non-volatile memory, or a combination thereof. A given processor 130 of local controller 20 may be configured as typically done, and in some embodiments may be configured, for example, to perform operations associated with local controller 20 and one or more of the modules thereof (e.g., within memory 140 or elsewhere). In some cases, memory 140 may be configured to be utilized, for example, for processor workspace (e.g., for one or more processors 130) and/or to store media, programs, applications, and/or content on the local controller 20 on a temporary or permanent basis.

The one or more modules stored in memory 140 can be accessed and executed, for example, by the one or more processors 130 of the local controller 20. In accordance with some embodiments, a given module of memory 140 can be implemented in any suitable standard and/or custom/proprietary programming language, such as, for example C, C++, objective C, JavaScript, and/or any other suitable custom or proprietary instruction sets, as will be apparent in light of this disclosure. The modules of memory 140 can be encoded, for example, on a machine-readable medium that, when executed by one or more processors 130, carries out the functionality of computing device 100, in part or in whole. The computer-readable medium may be, for example, a hard drive, a compact disk, a memory stick, a server, or any suitable non-transitory computer/computing device memory that includes executable instructions, or a plurality or combination of such memories. Other embodiments can be implemented, for instance, with gate-level logic or an application-specific integrated circuit (ASIC) or chip set or other such purpose-built logic. Some embodiments can be implemented with a microcontroller having input/output capability (e.g., inputs for receiving user inputs; outputs for directing other components) and a number of embedded routines for carrying out the device functionality. In a more general sense, the functional modules of memory 140 (e.g., such as operating system (OS) 142, graphic user interface (GUI) 143, and/or one or more applications 144, each discussed below) can be implemented in hardware, software, and/or firmware, as desired for a given target application or end-use. The memory 140 may include an operating system (OS) 142. The OS 142 can be implemented with any suitable OS, mobile or otherwise, such as, for example, Android OS from Google, Inc.; iOS from Apple, Inc.; BlackBerry OS from BlackBerry Ltd.; Windows Phone OS from Microsoft Corp; Palm OS/Garnet OS from Palm, Inc.; an open source OS, such as Symbian OS; and/or a combination of any one or more thereof. As will be appreciated in light of this disclosure, OS 142 may be configured, for example, to aid with the lighting controls to provide predictive light characteristic settings to be projected by the light emitting devices 50.

The memory 140 may also include at least one module for saved light settings 145. The saved light settings 145 includes modules of memory for storing at least one of said initial setting for the lighting characteristics, said user adjustments to the lighting characteristics, and said predictive light characteristic light settings. For example, the initial light settings, e.g., lights settings consistent with the human circadian rhythm, can be saved in an initial light setting module 147. The user adjustments to the lighting characteristics, which are employed by the remote light setting computing device, e.g., machine learning device 80, to provide the predictive light characteristic settings can be saved in a user data module 146. The predictive light characteristic settings received by the local controller 20 can be stored in a predictive light characteristic module 148.

In accordance with some embodiments, local controller 20 may include a graphic user interface (GUI) module 143. In some cases, GUI 143 can be implemented in memory 140.

The memory 140 may have stored therein (or otherwise have access to) one or more applications 144. In some instances, the local controller 20 may be configured to receive input data and/or transmit output data, for example, via one or more applications 144 stored in memory 140, such as a light characteristic selection application 141. The light characteristic selection application 141 can provide a plurality of selectable light function settings on the graphic user interface of the display 21, e.g., a color wheel 16c, dimming scale 16b, and color temperature scale 16c, as depicted in FIG. 8. The light characteristic selection application 141 correlates selection of these selectable light function settings to the light being emitted by the light emitting devices. In addition to the above noted scales, the light characteristic selection application also provides for the selection of lighting to be activated, in scenes 19, e.g., a bedroom, as well as providing for the selection of lighting form factors 18, time periods for ON and OFF lightings 17a, 17b. The light characteristic selection application 141 correlates selection of these selectable light function settings to the light being emitted by the light emitting devices.

The light characteristic selection application 141 can also employ the selected light characteristics as the initial light characteristic setting, which could be saved in the initial light setting module 147 of the saved light settings 145 in the memory 140. This can provide the baseline light characteristics for lighting, i.e., light emitted by the light emitting devices 50, which is actuated by the user, e.g., through the light switch 25.

The light characteristic selection application 141 can also determine if the selected light characteristics deviate from the initial light characteristic settings in a manner that would provide for light adjustments, which could be saved as user data 146 and sent via the user data transmitter 136 to the remote light setting computing device, i.e., machine learning device 80 and cloud computing environment 75. As described above, the remote predictive light setting computing system analyzes the user data, i.e., lighting adjustments by the user, and provides a predictive lighting characteristic setting. The predictive light characteristic setting is sent from the remote light setting computing device back to the local controller and saved in the predictive light characteristic setting 148 module of the save light settings 145 of the memory 140. The light characteristic selection application 141 may also provide that when the user actuates lighting through the switch 25, that the predictive light characteristic setting provides the lighting characteristics of the light emitted by the light emitting devices 50 in response to activation by the switch 25.

In some embodiments, the local controller 20 may also include at least one sensor 41 for detecting light, e.g., an ambient light sensor 163. The ambient light sensor 163 can detect light in the area of the light emitting devices 50. The ambient light that is measured can function as an environmental factor base input to the lighting model for providing a predictive light characteristic light setting. The ambient light is recorded by the at least one sensor 41, and sent from the local controller 20 with the user data for analysis by the light setting computing device, i.e., machine learning device 80 and cloud computing environment 75.

Referring to FIG. 9, the local control may also include a controller 120. A given controller 120 may be configured to output one or more control signals to control any one or more of the various components/modules of computing device 100 and may do so, for example, based on wired and/or wireless input received from a given local source (e.g., such as on-board memory 140) and/or remote source. In accordance with some embodiments, a given controller 120 may host one or more control modules and can be programmed or otherwise configured to output one or more control signals. For example, the controller 120 can be a microcontroller for controlling content through the communications module 135 including the transmission of the predictive light characteristic settings to the light emitting devices 50 using the predictive light characteristic setting transmitter 136. The microcontroller 120 may command the transmission of the predictive light characteristic settings to the light emitting device 50 in response to the user's actuation of the switch 25. The controller 120 may also facilitate transmission of the user data to the remote predictive light setting computing system that provides the predictive light characteristic setting, as well as receipt of the predictive light characteristic setting at the local controller 20 from the remote predictive light setting computing system.

It is noted that the local controller 20 described above is only one example of what can be used with the methods and systems and computer program products of the present disclosure, and it is not intended that the local controller 20 be limited to only the above description. For example, the local controller 20 may further include other components, such as microphones 163, which could be employed in voice commands, and one or more loudspeakers 170 or other audio output devices. Loudspeaker(s) 170 can be, for example, a speaker or any other device capable of producing sound from an audio data signal, such as an affirmation single. As illustrated in FIG. 9, the aforementioned elements of the local controller device 20 may be interconnected with a communications bus 105.

Figure 10:
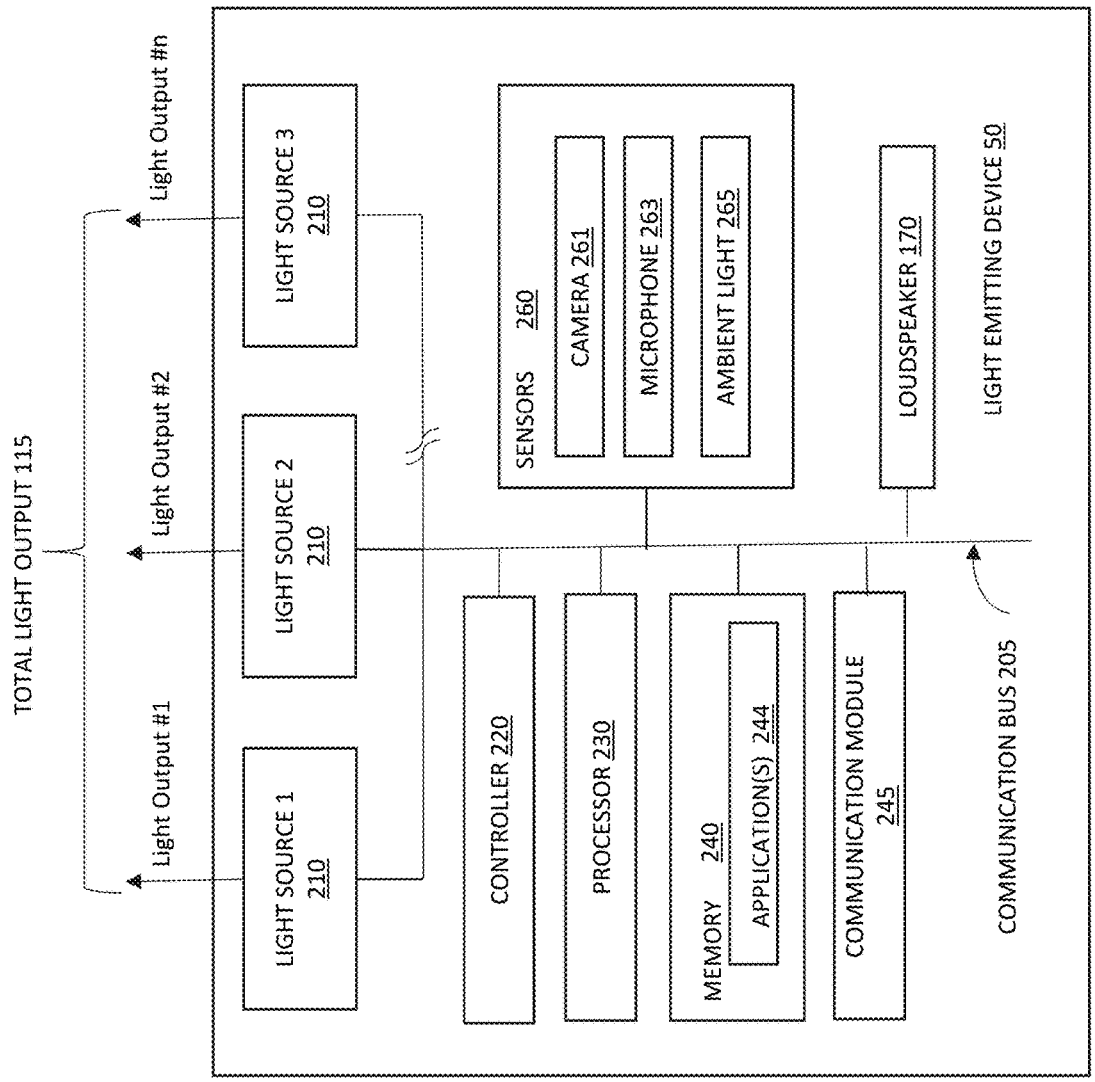
FIG. 10 is an illustration (block diagram) of an exemplary luminaire system that can work in communication with the system for controlling lighting using predictive light characteristics, in accordance with one embodiment of the present disclosure.
Figure 11:
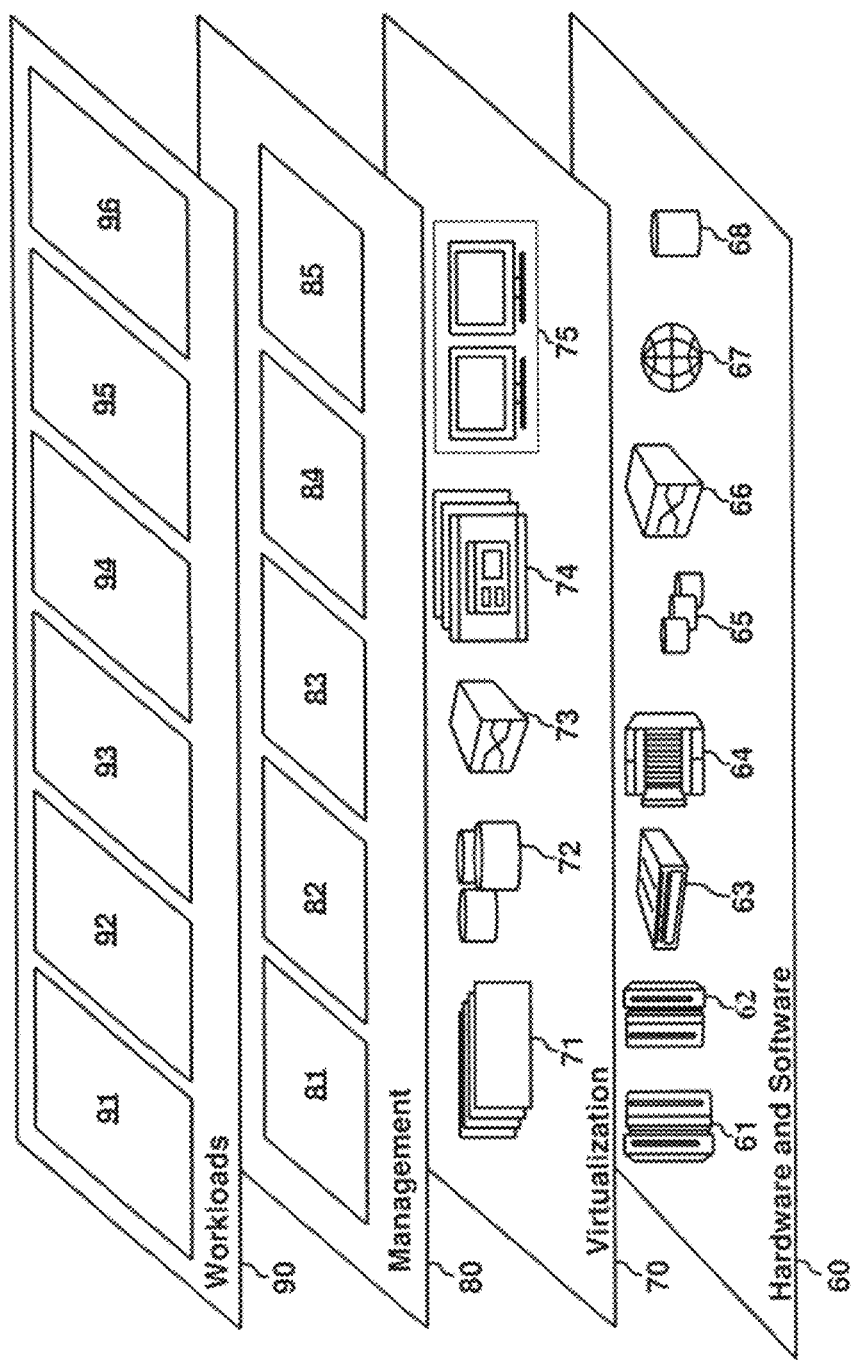
FIG. 11 is an illustration depicting abstraction model layers in a cloud computing environment, in accordance with one embodiment of the present disclosure.

FIG. 10 is a block diagram depicting an exemplary light emitting device 50 (also referred to as luminaire) that can work in communication with the system for lighting control that is described with reference to FIG. 1, and the method of light control that is described with reference to FIG. 2. As can be seen, the light emitting device 50 may include one or more light sources 210 that each provide corresponding light output. The number n of light sources 210 for a given light emitting device 50 can be customized as desired for a given target application or end-use. The light sources 210 and componentry of the light emitting device 50 will be described in more detail herein. However, note that the light emitting device 50 may include additional or alternative componentry based on the specific configuration used. For example, in the case of the light emitting device 50 including solid-state light sources 210, the light emitting device 50 may include componentry, such as at least one driver, modulator, digital to analog (DAC) converter (not shown), just to name some additional example componentry. Also note that although the componentry (e.g., controller 220, processor 230, etc.) is shown as being within the box representing the light emitting device 50, such componentry need not be physically located within the housing of the light emitting device 50. In some embodiments, some or all (or alternative) componentry shown in FIG. 10 may generally be a part of lighting system 100 as shown in FIG. 1 and may be used to control multiple luminaires (e.g., control multiple light emitting devices 50 simultaneously).

In some embodiments, the light emitting devices 50 may include one or more solid-state light sources 210. A given solid-state light source may include one or more solid-state emitters, which may be any of a wide range of semiconductor light source devices, such as, for example: a light-emitting diode (LED); (2) an organic light-emitting diode (OLED); (3) a polymer light-emitting diode (PLED); and/or (4) a combination of any one or more thereof. In some embodiments, a given solid-state emitter may be configured for color-tunable emissions. For instance, in some cases, a given solid-state emitter may be a multi-color (e.g., bi-color, tri-color, etc.) semiconductor light source configured for a combination of emissions, such as: (1) red-green-blue (RGB); (2) red-green-blue-yellow (RGBY); (3) red-green-blue-white (RGBW); (4) dual-white; and/or (5) a combination of any one or more thereof. In some embodiments, luminaire 200 may include other light sources 210 in addition to or in the alternative of solid-state light sources 210, such as incandescent or fluorescent lighting, for example. The quantity and arrangement of lighting sources 210 utilized for each luminaire may be customized as desired for a given target application or end-use.

The light emitting devices 50 may include at least one controller 220, at least one processor 230, and/or memory 240. Controller(s) 220 may be configured to be operatively coupled (e.g., via a communication bus or other suitable interconnect) with light sources 210 or corresponding componentry, such as the light source drivers (not shown), to control the light output provided therefrom. Note that the light output from each light source 210 creates a total light output 215, in this example embodiment. In some embodiments, luminaire 200 may include a centralized controller 220 and/or processor 230 configured to control the total light output 215 of the entire system. In some such embodiments, the control of the light output may be wired and/or wireless, depending upon the given configuration. In some embodiments, light sources 210 of luminaire may be individually controlled. The controller 220 is in communication with the communication bus 205, hence receives signals from the local controller 20 through the communications module 250. The signals received from the local controller 20 can include information on lighting characteristics for light to be emitted from the light emitting devices, such as the initial light characteristics and/or predictive light characteristics.

The memory 240 used by the light emitting device 50 can be of any suitable type (e.g., RAM and/or ROM, or other suitable memory) and size, and in some cases may be implemented with volatile memory, non-volatile memory, or a combination thereof. A given processor 230 may be configured as typically done, and in some embodiments may be configured, for example, to perform operations associated with the light emitting device 50 or a given light source 210 and one or more of the modules thereof (e.g., within memory 240 or elsewhere). In some cases, memory 240 may be configured to be utilized, for example, for processor workspace (e.g., for one or more processors 230) and/or to store media, programs, applications 244, and/or content for luminaire 200 or system on a temporary or permanent basis.

The one or more modules stored in memory 240 can be accessed and executed, for example, by the one or more processors 230 of the light emitting device 50. In accordance with some embodiments, a given module of memory 240 can be implemented in any suitable standard and/or custom/proprietary programming language, such as, for example: (1) C; (2) C++; (3) objective C; (4) JavaScript; and/or (5) any other suitable custom or proprietary instruction sets, as will be apparent in light of this disclosure. The modules of memory 240 can be encoded, for example, on a machine-readable medium that, when executed by a processor 230, carries out the functionality of luminaire 200 or system, in part or in whole. The computer-readable medium may be, for example, a hard drive, a compact disk, a memory stick, a server, or any suitable non-transitory computer/computing device memory that includes executable instructions, or a plurality or combination of such memories. Other embodiments can be implemented, for instance, with gate-level logic or an application-specific integrated circuit (ASIC) or chip set or other such purpose-built logic. Some embodiments can be implemented with a microcontroller having input/output capability (e.g., inputs for receiving user inputs; outputs for directing other components) and a number of embedded routines for carrying out the device functionality. In a more general sense, the functional modules of memory 240 (e.g., one or more applications 242, discussed below) can be implemented in hardware, software, and/or firmware, as desired for a given target application or end-use.

In accordance with some embodiments, the memory 240 of the luminaire light emitting device 50 may have stored therein (or otherwise have access to) one or more applications 242. In some instances, a given luminaire light emitting device 50 may be configured to receive input, for example, via one or more applications 242 stored in memory 240. For instance, an example application 242 may allow a user to program or configure a light emitting device 50 to project light having characteristics consistent with a command via an initial light characteristic setting and/or predictive light characteristic setting, such as the light color, light intensity/dimming, or light temperature color.

In some embodiments, a given light emitting device 50 may include a communication module 250, which may be configured for wired (e.g., Universal Serial Bus or USB, Ethernet, FireWire, etc.) and/or wireless (e.g., Wi-Fi, Bluetooth, etc.) communication, as desired. In accordance with some embodiments, communication module 250 may be configured to communicate locally and/or remotely utilizing any of a wide range of wired and/or wireless communications protocols, including, for example: (1) a digital multiplexer (DMX) interface protocol; (2) a Wi-Fi protocol; (3) a Bluetooth protocol; (4) a digital addressable lighting interface (DALI) protocol; (5) a ZigBee protocol; and/or (6) a combination of any one or more thereof. It should be noted, however, that the present disclosure is not so limited to only these example communications protocols, as in a more general sense, and in accordance with some embodiments, any suitable communications protocol, wired and/or wireless, standard and/or custom/proprietary, may be utilized by communication module 250, as desired for a given target application or end-use. In some instances, communication module 250 may be configured to facilitate inter-system communication between the light emitting device 50 and/or communication between the light emitting devices 50 and at least one of the local controller 20, user interface 40, and/or the remote predictive light setting computing system including a machine learning device 80 and cloud computing environment 75.

In accordance with some embodiments, a given light emitting device 50 may include one or more optional sensors 260. In some embodiments, a given light emitting device 50 may optionally include at least one camera 261 (or image capture device), microphone 263 (or sound capture device), ambient light sensor 265, motion sensor 267, 3-dimensional (3D) depth sensor 269, and/or any other suitable sensor to, for example, implement the techniques variously described herein. When included, sensor(s) 260 may be configured as typically done. In another example, microphone 263 may be configured to detect voice commands used to control the light emitting device 50. In any case, the sensor(s) 260 of a given light emitting device 50 may include componentry as desired for a given target application or end-use. Also, it should be noted that the present disclosure is not so limited only to the example optional sensors 260 shown, as additional and/or different sensors 260 may be provided, as desired for a given target application or end-use, in accordance with some other embodiments.

In accordance with some embodiments, a given light emitting device 50 may include one or more loudspeakers 270 or other audio output devices. Loudspeaker(s) 270 can be, for example, a speaker or any other device capable of producing sound from an audio data signal, in accordance with some embodiments. Loudspeaker(s) 270 may be programmed using any suitable techniques and they may be configured to output audio related to the lighting control techniques variously described herein. For example, controller 220 and/or processor 230 may be configured to control audio output of the loudspeaker(s) 270 to provide audio feedback as to whether an attempted command has been recognized or provide audio feedback relating to the specific command detected or the resulting change in light output (e.g., dimming lights by 10%, changing light color to red, etc.). Numerous configurations and variations on light emitting devices 50 will be apparent in light of this disclosure.

It is understood that this disclosure includes a detailed description on cloud computing, implementation of the teachings recited herein are not limited to a cloud computing environment. Rather, embodiments of the present invention are capable of being implemented in conjunction with any other type of computing environment now known or later developed.

The methods of the present disclosure may be practiced using a cloud computing environment. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 7, illustrative cloud computing environment 75 is depicted. As shown, cloud computing environment 75 includes one or more cloud computing nodes 110 with which computing devices used by cloud consumers, such as, for example, the machine learning device 80, the local controller 20, and the user terminal 40, as well as other mobile and/or wearable electronic devices, desktop computer, laptop computer, and/or automobile computer system may communicate. Nodes 110 may communicate with one another. They may be grouped (not shown) physically or virtually, in one or more networks, such as Private, Community, Public, or Hybrid clouds as described hereinabove, or a combination thereof. This allows cloud computing environment 75 to offer infrastructure, platforms and/or software as services for which a cloud consumer does not need to maintain resources on a local computing device. It is understood that the types of computing devices 20, 40, and 80 shown in FIG. 7 are intended to be illustrative only and that computing nodes 110 and cloud computing environment 75 can communicate with any type of computerized device over any type of network and/or network addressable connection (e.g., using a web browser).

Referring now to FIG. 10, a set of functional abstraction layers provided by cloud computing environment 75 (FIG. 1) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and the remote predictive light setting computer system 75 for providing a predictive light characteristic light setting in response to an environment factor based input, which is described with reference to FIGS. 1-9.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a method, system and computer program product for controlling lighting, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method of lighting control comprising:
setting an initial setting for characteristics for light emitted by lighting devices, wherein the initial setting for the characteristics for light comprises light temperature lighting characteristics matching a human circadian rhythm and light intensity lighting characteristic that decrease during daylight relative to at least one of the morning and the evening, and the initial setting for the characteristic of light comprises a light dimming selection setting corresponding to a scene setting for a location of the lighting devices;
recording user adjustments to the light temperature lighting characteristic matched to the human circadian rhythm over an entirety of a 24 hour period of a day, the light intensity lighting characteristics and the light dimming as user data;
analysis of the user data including the user adjustments with a remote light setting computing system to determine a lighting model for providing a predictive light characteristic light setting that provides for lighting adjustments from the lighting characteristics matching the human circadian rhythm and the light dimming selection setting corresponding to the scene in response to an environment factor based input, the remote light setting computing system employing machine learning remotely from the lighting devices for providing the lighting model;
inputting environmental factors including sun lighting, season and weather into the model produced by the remote light setting computing system to provide a predictive light characteristic setting, the predictive light characteristic setting taking into account the circadian rhythm and the environmental factors with additional lighting adjustments to treat seasonal affective disorder (SAD);
sending the predictive light characteristic setting from the remote light setting computing system to a local controller, the local controller for sending commands to control light emissions from the lighting devices; and
adjusting light being emitted from the light emitting devices to the predictive light characteristics using the local controller in response to a user lighting request over an entirety of the 24 hour period of the day.

2. The method of claim 1, wherein the lighting devices include a light source provided by light emitting diodes (LEDs).

3. The method of claim 1, wherein the characteristics for light of said initial setting further include a characteristic selected from the group consisting of light color, light intensity, and combinations thereof.

4. The method of claim 1, wherein the user adjustments to the characteristics for light includes calendar based automatic adjustments, end user manual adjustments, or a combination thereof.

5. The method of claim 1, wherein the user adjustments to the characteristics for light includes user adjustments in lighting in response to a difference in lighting between sun filled days and rainy days.

6. The method of claim 1, wherein the user adjustments to the characteristics for light include predictive lighting in response to a calendar event, on demand prescription lighting or a combination thereof.

7. The method of claim 1, wherein the analysis of the user data with the remote light setting computing system to determine the lighting model comprises a machine learning method is selected from the group consisting of decision tree learning, association rule learning, artificial neural networks, deep learning, inductive logic programming, support vector machines, clustering analysis, bayesian networks, reinforcement learning, representation learning, similarity and metric learning, sparse dictionary learning, genetic algorithms, rule-based machine learning, learning classifier systems, and combinations thereof.

8. The method of claim 1, wherein the environmental factors are selected from the group consisting of time, calendar date, weather and combinations thereof.

9. The method of claim 1, wherein the machine learning remotely from the lighting devices comprises providing a machine learning engine through a cloud environment.

10. A system for controlling lighting comprising:
  a local controller for sending commands to control light emissions from at least one light emitting device, and for recording user adjustments to characteristics of said light emissions from said at least one light emitting device from an initial setting as user data, the initial setting for lighting characteristics comprising light temperature lighting characteristics matching a human circadian rhythm and light intensity lighting characteristics that decrease during daylight relative to at least one of the morning and the evening over an entirety of a 24 hour period of a day for the initial setting, and the initial setting for the characteristics of light comprises a light dimming selection setting corresponding to a scene setting for a location of the lighting devices; and
  a remote light setting computing device for analyzing the user data including the user adjustments received from the local controller, the remote light setting computing device analyzing the user data using machine learning calculations remotely processed from the at least one lighting device to provide a lighting model for providing a predictive light characteristic light setting that provides for lighting adjustments from the light temperature lighting characteristics matching the human circadian rhythm and the light dimming selection setting corresponding to the scene in response to an environment factor based input including sun lighting, season and weather, the predictive light characteristic setting taking into account the circadian rhythm and the environmental factors with lighting adjustments to treat seasonal affective disorder (SAD), wherein the remote light setting computing device transmits the predictive light characteristic light setting to the local controller for said commands to control light emissions from the at least one light emitting device over an entirety of a 24 hour period of a day for light adjustments.

11. The system of claim 10 further comprising an application run on a mobile device as a first user interface to entering the initial setting for the characteristics of said light emissions from said at least one light emitting device.

12. The system of claim 11, wherein the application run on the mobile device includes a second user interface for entering said user adjustments to the characteristics of said light emissions from said at least one light emitting device.

13. The system of claim 10, wherein the remote light setting computing device comprises a machine learning device in communication with the local controller using a cloud computing environment, wherein the machine learning device employs a leaning method to provide the lighting model for providing a predictive light characteristic light setting, the learning method selected from the group consisting of decision tree learning, association rule learning, artificial neural networks, deep learning, inductive logic programming, support vector machines, clustering analysis, bayesian networks, reinforcement learning, representation learning, similarity and metric learning, sparse dictionary learning, genetic algorithms, rule-based machine learning, learning classifier systems, and combinations thereof.

14. The system of claim 10, wherein the local controller comprises:
  an interface for entering at least one of the initial setting for the characteristics of said light emissions from said at least one light emitting device, and entering said user adjustments to the characteristics of said light emissions from said at least one light emitting device;
  a communications module for providing wireless communication from the local controller to the remote light setting computing device for receipt of predictive light characteristic light settings, and sending user adjustments to the remote light setting computing device, wherein the communications module also provide wireless communication to the light emitting devices; and
  a microcontroller for controlling content through the communications module including the transmission of the predictive light characteristic light settings to the light emitting devices.

15. The system of claim 10, wherein the user interface of the local controller comprises at least one of a display screen and a keypad for said entering said at least one of the initial setting for the lighting characteristics and said user adjustments to the lighting characteristics.

16. The system of claim 10, wherein the local controller further comprises memory for storing at least one of said initial setting for the lighting characteristics, said user adjustments to the lighting characteristics, and said predictive light characteristic light settings.

17. The system of claim 10, wherein the local controller includes a rocker switch for an ON and OFF light switch, and the local controller has a housing for wall mount installation.

18. The system of claim 10, wherein the local controller includes at least one sensor for detecting light.

19. A non-transitory computer readable storage medium including contents that are configured to cause a computer to perform a method for controlling lighting, the method comprising:
  setting an initial setting for lighting characteristics for light emitted by lighting devices, wherein the initial setting for lighting characteristics comprises light temperature lighting characteristics matching a human circadian rhythm and light intensity characteristics that decrease during daylight relative to at least one of the morning and the evening, and the initial setting for the characteristics of light comprises a light dimming selection setting corresponding to a scene setting for a location of the lighting devices;
  recording user adjustments to the light temperature lighting characteristic matched to the human circadian rhythm over an entirety of a 24 hour period of a day, the light intensity lighting characteristics and the light dimming from the initial setting as user data;
  analysis of the user data including the user adjustments with a remote light setting computing system to determine a lighting model that provides for lighting adjustments from the light temperature lighting characteristics matching the human circadian rhythm and the light dimming selection setting corresponding to the scene for providing a predictive light characteristic light setting in response to an environment factor based input, the remote light setting computing system employing machine learning remotely from the lighting devices for providing the lighting model;
  inputting environmental factors including sun lighting, season and weather into the model produced by the remote light setting computing system to provide a predictive light characteristic setting, the predictive light characteristic setting taking into account the circadian rhythm and the environmental factors with lighting adjustments to treat seasonal affective disorder (SAD);
  sending the predictive light characteristic setting from the remote light setting computing system to a local controller, the local controller for sending commands to control light emissions from the lighting devices; and adjusting light being emitted from the light emitting devices to the predictive light characteristics using the local controller in response to a user lighting request over the entirety of the 24 hour period of a day.

* * * * *